(12) United States Patent
Malik et al.

(10) Patent No.: US 7,622,191 B2
(45) Date of Patent: Nov. 24, 2009

(54) TITANIA-BASED COATING FOR CAPILLARY MICROEXTRACTION

(75) Inventors: Abdul Malik, Tampa, FL (US); Tae-Young Kim, Tampa, FL (US)

(73) Assignee: University of South Florida, Tampa, FL (US)

( * ) Notice: Subject to any disclaimer, the term of this patent is extended or adjusted under 35 U.S.C. 154(b) by 513 days.

(21) Appl. No.: 11/161,005

(22) Filed: Jul. 19, 2005

(65) Prior Publication Data
US 2006/0013982 A1    Jan. 19, 2006

Related U.S. Application Data

(60) Provisional application No. 60/521,901, filed on Jul. 19, 2004.

(51) Int. Cl.
*B32B 15/00* (2006.01)

(52) U.S. Cl. .................. 428/432; 438/446; 438/450; 438/701; 438/702

(58) Field of Classification Search ............... None
See application file for complete search history.

(56) References Cited

U.S. PATENT DOCUMENTS

| | | | |
|---|---|---|---|
| 4,509,964 A | 4/1985 | Hubball et al. | |
| 4,966,785 A | 10/1990 | Springston | |
| 5,128,291 A | 7/1992 | Wax et al. | |
| 5,192,406 A | 3/1993 | Woolley | |
| 5,262,052 A | 11/1993 | Rossiter et al. | |
| 5,270,027 A | 12/1993 | Balducci et al. | |
| 5,308,495 A | 5/1994 | Avnir et al. | |
| 5,589,396 A | 12/1996 | Frye et al. | |
| 5,624,875 A | 4/1997 | Nakanishi et al. | |
| 5,637,135 A | 6/1997 | Ottenstein et al. | |
| 5,821,186 A * | 10/1998 | Collins ........................ 502/8 | |
| 5,869,152 A | 2/1999 | Colon | |
| 6,344,242 B1 | 2/2002 | Stolk et al. | |
| 6,613,234 B2 | 9/2003 | Voute et al. | |
| 6,759,126 B1 | 7/2004 | Malik et al. | |
| 6,783,680 B2 | 8/2004 | Malik | |
| 2003/0075447 A1 | 4/2003 | Malik et al. | |

(Continued)

FOREIGN PATENT DOCUMENTS

WO    WO 00/11463    3/2000

OTHER PUBLICATIONS

Zeng, Z. et al. "Solid-Phase Microextraction Using Fused-Silica Fibers Coated with Sol-Gel-Derived Hydroxy-Crown Ether", *Anal. Chem.*, 73, 2429-2436 (2001).

(Continued)

*Primary Examiner*—Timothy M Speer
(74) *Attorney, Agent, or Firm*—Saliwanchik, Lloyd & Saliwanchik

(57) ABSTRACT

A method is presented describing in situ preparation of the titania-based sol-gel PDMS coating and its immobilization on the inner surface of a fused silica microextraction capillary. Sol-gel titania-poly (dimethylsiloxane) ($TiO_2$-PDMS) coating was developed for capillary microextraction (CME) to perform on-line preconcentration and HPLC analysis of trace impurities in aqueous samples. The sol-gel titania-based coatings demonstrated strong pH stability and enhanced extraction capability over other commercially availble GC coatings. Extraction characteristics of a sol-gel titania-PDMS capillary remained practically unchanged after continuous rinsing with a 0.1 M NaOH solution (pH=13) for 12 hours.

7 Claims, 12 Drawing Sheets

U.S. PATENT DOCUMENTS

2004/0129141 A1 7/2004 Malik et al.
2005/0106068 A1 5/2005 Malik et al.

OTHER PUBLICATIONS

Zhang, J. et al. "Development of the Personal Aldehydes and Ketones Sampler Based upon DNSH Derivatization on Solid Sorbent", *Environ. Sci. Technol.*, 34, 2601-2607 (2000).

Zhang, Z. et al. "Solid-Phase Microextraction", *Anal. Chem.* 66, 844A-853A (1994).

U.S. Appl. No. 10/704,766, filed Nov. 10, 2003, Malik et al.

Aichholz, R., "Preparation of Glass Capillary Columns Coated with OH-Terminated (3,3,3-Trifluoropropyl) Methyl Polysiloxane (PS 184.5)", *Journal of High Resolution Chromatography*, 13, 71-73 (1990).

Albin, M. et al. "Sensitivity Enhancement for Capillary Electrophoresis", *Analytical Chemistry*, 65, 489-497A (1993).

Alltech, *Chromatography Catalog*, 172 (1997).

Altgelt, K. et al., *Chromatography in Petroleum Analysis*, Marcel Dekker, Inc., New York and Basel (1979).

Alhooshani, K. et al. "Sol-Gel Approach to in situ Creation of High pH-resistant surface-bonded Organic-Inorganic Hybrid Zirconia Coating for Capillary Microextraction (in-tube SPME)" *Journal of Chromatography A*, 1065, 1-14 (2005).

Belardi, R. et al., "The Application of Chemically Modified Fused Silica Fibers in the Extraction of Organics from Water Matrix Samples and their Rapid Transfer to Capillary Columns", *Water Pollut. Res. J. Can.*, 24, 179-191 (1989).

Berezkin, V.G. et al., "Capillary Columns with Several Layers of Different Immobilized Stationary Phases", *J. Anal. Chem.—USSR*, 47, 600-604 (1992).

Berezkin, V.G. et al., *Gas Chromatography in Air Pollution Analysis*, Elsevier, Amsterdam—Oxford—New York—Tokyo, Chapter 8, 165-207 (1991).

Bigham, S. et al. "Sol-Gel Capillary Microextraction", *Anal. Chem.* 74, 752-761 (2002).

Blau, K. et al., eds., *Handbook of Derivatives for Chromatography*, 2$^{nd}$ ed., John Wiley & Sons, Chichester—New York—Brisbane—Toronto—Singapore, 1-30 (1993).

Blomberg, L. et al., "Modification of Glass Capillary Columns by Cyclic (3,3,3-Trifluoropropyl)methylsiloxanes", *Journal of HRC & CC*, 3, 527-528 (1980).

Brinker, C.J. et al., *Sol-Gel Science: The Physics and Chemistry of Sol-Gel Processing*, Academic Press, San Diego—New York—Boston—London—Sydney—Tokyo—Toronto, 97-233 (1990).

Britz-McKibbin, P. et al. "On-Line Focusing of Flavin Derivative Using Dynamic pH Junction-Sweeping Capillary Electrophoresis with Laser-Induced Fluorescence Detection", *Anal. Chem.*, 74, 3736-3743 (2002).

Britz-McKibbin, P. et al. "Selective Focusing of Catecholamines and Weakly Acidic Compounds by Capillary Electrophoresis Using a Dynamic pH Junction", *Anal. Chem.*, 72, 1242-1252 (2000).

Brown, P. B. et al. "The Separation and the Characterization of Long Chain Fatty Acids and Their Derivatives by Reversed Phase High Performance Liquid Chromatography", *Analytical Chemistry*, 21, 193-208, (1989).

Cao, C.-X. et al. "Stacking Ionizable Analytes in a Sample Matrix with High Salt by a Transient Moving Chemical Reaction Boundary Method in Capillary Zone Electrophoresis", *Anal. Chem.* 74, 4167-4174 (2002).

Chen, Z. et al. "Chemically Modified chiral monolithic Silica Column Prepared by a Sol-Gel Process for Enantiomeric Separation by Micro High-Performanc Liquid Chromatography", *J. Chromatogra.*, 942, 83-91 (2002).

Chien, R.-L. et al. "On-Column Sample Concentration Using Field Amplification in CZE", *Anal. Chem.*, 64, 489A-496A (1992).

Chien, R.-L et al. "Sample Stacking of an Extremely Large Injection Volume in High-Performance Capillary Electrophoresis", *Anal. Chem.*, 64, 1046-1050 (1992).

Chun, M.-S. et al. "Protein Analysis with Large Volume Sample Stacking with an Electrosmotic Flow Pump: A Potential Approach for Proteomics", *Microchem. J.*, 70, 247-253 (2001).

Church, M. N. et al. "Transient Isotachophoretic-Electrophoretic Separations of Lanthanides with Indirect Laser-Induced Fluorescence Detection", *Anal. Chem.*, 70, 2475-2480 (1998).

Cifuentes, A. et al. "Capillary Isoelectric Focusing of Erythropoietin Glycoforms and its Comparison with Flat-bed Isoelectric Focusing and Capillary Zone Electrophoresis", *J. Chromatogra.*, 830, 453-463 (1999).

Clarke, N. J. et al. "Capillary Isoelectric Focusing-Mass Spectrometry: Analysis of Protein Mixtures from Human Body Fluids", *Biomed. Chromatogr.*, 16, 287-297 (2002).

Clifford, A. A. "Introduction to Supercritical Fluid Extraction in Analytical Science", in *Supercritical Fluid Extraction and its Use in Chromatographic Sample Preparation*, Westwood, S. A. (ed.), 1-38 (1993).

Collinson, M. M. et al. "Sol-gels and Electochemistry", *Analytical Chemistry*, 72, 702A-709A (2000).

Coulibaly, K. et al. "An overview of Solid-Phase Extraction of Food Flavor Compounds and Chemical Residues", *Food Rev. Int.*, 12, 131-151 (1996).

Deng, Y. et al. "Chip-Based Quantitative Capillary Electrophoresis/Mass Spectrometry Determination of Drugs in Human Plasma", *Anal. Chem.*, 73, 1432-1439 (2001).

Ettre, L.S. et al., *Basic Relationships of Gas Chromatography*, Advanstar, Cleveland, OH, 1-34 (1993).

Ettre, L.S., "Performance of Open Tubular Columns as a Function of Tube Diameter and Liquid Phase Film Thickness", *Chromatographia*, 18, 477-488(1984).

Ferioli, V. et al., "High-Performance Liquid Chromatography of Dihydroxyacetone as its bis-2,4-Dinitrophenylhydrazone Derivative," *Chromatographia*, 41, 61-65 (1995).

Furton, K. G. et al. "The Use of Solid-Phase Microextraction-Gas Chromatography in Forensic Analysis", *Journal of Chromatographic Science*, 38, 297-306, (2000).

Guo, Y. et al. "A Stationary Phase for Open Tubular Liquid Chromatography and Electrochromatography Using Sol-Gel Technology", *Anal. Chem.*, 67, 2511-2516 (1995).

Hamlet, C. et al., "Novel Sol-Gel Dendrimer Coatings for Ultra-Trace Environmental Analysis by Capillary Microextraction Coupled to Gas Chromatography", *5$^{th}$ International Symposium on Advances in Extraction Technologies*, St. Pete Beach, FL (Mar. 5-7, 2003).

Hartmann, H. et al., "Trace Determination of Pesticides in Water by Coated Capillary Micro Extraction (CCME) and Reversed-Phase High Performance Liquid Chromatography", *Fresenius Environmental Bulletin*, 7, 96-103 (1998).

Haruvy, Y. et al., "Sol-Gel Replication of Microoptical Elements and Arrays", *Chem. Mater.*, 9, 2604-2615 (1997).

Hayes, J. D. et al. "Sol-Gel Process Mediated Advanced Column Technology for Microcolumn Separations", *18$^{th}$ International Symposium on Capillary Chromatogr.*, 1, 496-504 (1996).

Hayes, J.D. et al., "Sol-Gel Chemistry-Based Ucon-Coated Columns for Capillary Electrophoresis", *J. Chromatogr. B*, 695, 3-13 (1997).

Hayes, J.D. et al., "Sol-Gel Monolithic Columns with Reversed Electroosmotic Flow for Capillary Electrochromatography", *Anal. Chem.*, 72, 4090-4099 (2000).

Hayes, J.D. et al., "Sol-Gel Open Tubular ODS Columns with Reversed Electroosmotic Flow for Capillary Electrochromatography", *Anal. Chem.*, 73, 987-996 (2001).

Hiraoka, A. et al. "One-Step Capillary Isoelectric Focusing of th Proteins in Cerebrospinal Fluid and Serum of Patients with Neurological Disorders", *J. Chromatogr. A*, 961, 147-153 (2002).

Hjertén, S. et al. "Adaptation of the Equipment for High-Performance Electrophoresis to Isoelectric Focusing", *J. Chromatogr.*, 346, 265-270 (1985).

Huang, M. et al. "Charged Suface Coatings for Capillary Electrophoresis", *J. Microcol.*, 5, 199-205 (1993).

Janák, K. et al., "Static Coating of Capillary Columns by Means of Liquefied Gases", *Journal of High Resolution Chromatography & Chromatography Cummunications*, 8, 843-847 (1985).

Kabir, A. et al. "Capillary Microextraction on Sol-Gel Dendrimer Coatings", *J. Chromatogr. A*, 1034, 1-11 (2004).

Kabir, A. et al. "Parts per Quadrillion Level Ultra-Trace Determination of Polar and Nonpolar Compounds via Solvent-Free Capillary Microextraction on Surface-bonded Sol-gel Polytetrahydrofuran Coating and Gas Chromatography-Flame Ionization Detection", *J. Chromatogr. A*, 1047, 1-13 (2004).

Kameoka, J. et al. "A Polymeric Microfluidic Chip for CE/MS Determination of Small Molecules", *Anal. Chem.*, 73, 1935-1941 (2001).

Kataoka, H. et al. "Simple and Rapid Determination of Amphetamine, Methamphetamine, and Their Methylenedioxy Derivatives in Urine by Automated In-Tube Solid-Phase Microextraction Coupled with Liquid Chromatography-Electrospray Ionization Mass Spectrometry", *Journal of Analytical Toxicology*, 24, 257-265 (2000).

Katoka, H. et al., "Automated In-Tube Solid-Phase Microextraction Coupled with Liquid Chromatography/Electrospray Ionization Mass Spectrometry for the Determination of β-Blockers and Metabolites in Urine and Serum Samples", *Anal. Chem.*, 71, 4237-4244 (1999).

Kim, J-B. et al. "On-line Sample Concentration in Micellar Electrokinetic Chromatography Using Cationic Surfactants", *J. Chromatogr. A*, 816, 123-130 (2001).

Kim, T-Y. et al. "High pH-resistant, Surface-Bonded Sol-Gel Titania Hybrid Organic-Inorganic Coating for Effective On-Line Hyphenation of Capillary Microextraction (In-tube Solid Phase Microextraction) with High-Performance Liquid Chromatography", *J. Chromatogr. A*, 1047, 165-174 (2004).

Koivusalmi, E. et al., "Quantitative RP-HPLC Determination of Some Aldehydes and Hydroxyaldehydes as Their 2,4-Dinitrophenylhydrazone Derivatives", *Anal. Chem.*, 71, 86-91 (1999).

Lee, M. L. et al. "Fused Silica Capillary Column Technology for Gas Chromatography", *J. Chromatog. Sci.*, 22, 136-142 (1984).

Li, W. et al. "Positively Charged Sol-Gel Coatings for On-Line Preconcentration of Amino Acids in Capillary Electrophoresis", *Anal. Chem.* 76, 218-227 (2004).

Lichtenberg, J. et al. "Sample Preconcentration by Field Amplification Stacking for Microchip-Based Capillary Electrophoresis", *Electrophoresis*, 22, 258-271 (2001).

Liu, Q. et al. "Poly(diallyldimethylammonium chloride) as a Cationic Coating for Capillary Electrophoresis", *J. Chromatogr. Sci*, 36, 126-130 (1997).

Locke, S. et al. "Techniques for the Optimization of Proteomic Strategies Based on Head Coumn Stacking Capillary Electrophoresis", *Anal. Chem.*, 72, 2684-2689 (2000).

Lopez-Avila, V. et al. "Evaluation of Soxtec Extraction Procedure fo Extacting Organic Compounds form Soils and Sediments", *J. AOAC International*, 76, 864-880 (1993).

MacKenzie, J. D. et al. "Hybrid Organic-Inorganic Materials, The Sol-Gel Approach" in *ACS Symposium Series*, 585, 226-236 (1995).

Majors, R. E. "Liquid Extraction Techniques for Sample Preparation", *LC GC International*, 10, 93-101 (1997).

Malik, A. et al., "Advanced Sol-gel Column Technology for Condensed-phase Microseparations", 25 Proc. *19th International Symposium on Capillary Chromatography and Electrophoresis*, Wintergreen, VA, USA, 54-55 (May 18-22, 1997).

Markides, K. E. et al. "Deactivation of Fused Silica Capillary Columns with Phenylhydrosiloxanes", *J. High Res. Chromatography & Chromatography Comm.*, 8, 378-384 (1985).

Martin, A. J. P. et al. "Displacement Electrophoresis", *Proc. Roy. Soc. Lond. A.*, 316, 493-514 (1970).

Minnich, M. M. et al. "Extraction Methods for Recovery of Volatile Organic Compounds from Fortified Dry Soils", *J. AOAC International*, 79, 1198-1204 (1996).

Mukherjee, S.P., "Supercritical Drying in Structural and Microstructural Evolution of Gels: A Critical Review", *Ultrastructure Processing of Advanced Ceramics*, J.D. MacKenzie and D.R. Ulrich, eds., John Wiley & Sons, New York—Chichester—Brisbane—Toronto—Singapore, 747-758 (1988).

Nawrocki, J. "Silica Surface Controversies, Strong Adsorption Sites Their Blockage and Removal. Part I", *Chromatogaphia*, 31, 177-205 (1991).

Novak, B. M. "Hybrid Nanocomposite Materials—Between Inorganic Glasses and Organic Polymers", *Advanced Materials*, 5, 422-433 (1993).

Núñez, O. et al. "Sample Stacking with Matrix Removal for the Determination of Paraquat, Diquat and Difenzoquat in Water by Capillary Electrophoresis", *J. Chromatogr. A*, 912, 353-361 (2001).

Oesterhelt, G. et al., "Analyse von Hydroxypivalaldehyd als Trimethylsilylderivat des Oxims mittels Gas-Chromatographie", *Fresenius Z. Anal. Chem.*, 321, Abstract (1985).

Ogden, M. W. et al. "Characterization of Fused-Silica Capillary Tubing By Contact Angle Measurements", *J. Chromatogr.*, 354, 7-18 (1986).

Palkar, V.R., "Sol-Gel Derived Nanostructured γ-Alumina Porous Spheres as an Adsorbent in Liquid Chromatography", *NanoStructured Materials*, 11, 369-374 (1999).

Palmer, J. et al. "A Universal Concept for Stacking Neutral Analytes in Micellar Capillary Electrophoresis", *Anal. Chem.*, 71, 1679-1687 (1999).

Palmer, J. et al. "Electrokinetic Injection for Stacking Neutral Analytes in Capillary and Microchip Electrophoresis", *Anal. Chem.*, 73, 725-731 (2001).

Palmer, J. et al. "Stacking Neutral Analytes in Capillary Electrokinetic Chromatographic with High-Salt Sample Matrixes", *Anal. Chem.*, 72, 1941-1943 (2000).

Pawliszyn, J., "Theory of Solid-Phase Microextraction," *Journal of Chromatographic Science*, 38, 270-278 (1999).

Quirino, J. P. et al. "Approaching a Million-Fold Sensitivity Increase in Capillary Electrophoresis with Direct Ultraviolet Detection: Cation-Selective Exhaustive Injection and Sweeping", *Anal. Chem.* 72, 1023-1030 (2000).

Quirino, J. P. et al. "Exceeding 5000-Fold Concentration of Dilute Analytes in Micellar Electrokinetic Chromatography", *Science*, 282, 465-468 (1998).

Quirino, J. P. et al. "On-line Concentration of Neutral Analytes for Micellar Electrokinetic Chromatography II. Reversed Electrode Polarity Stacking Mode", *J. Chromatogr. A*, 791, 255-267 (1997).

Quirino, J. P. et al. "On-line Concentration of Neutral Analytes for Micellar electrokinetic Chromatography 5. Field-Enhanced Sample Injection with Reversed Migrating Micelles," *Anal. Chem*, 70, 1893-1901 (1998).

Quirino, J. P. et al. "On-line Concentration of Neutral Analytes for Micellar Electrokinetic Chromatography I. Normal Stacking Mode", *J. Chromatogr. A*, 781, 119-128 (1997).

Quirino, J. P. et al. "Sweeping of Analyte Zones in Electrokinetic Chromotography", *Anal. Chem.* 71, 1638-1644 (1999).

Quirino, J. P. et al. "Sweeping with an Enhanced Electric Field of Neutral Analyte Zones in Electrokinetic Chromotography", *J. High Resol. Chromatogr.*, 22, 367-372 (1999).

Reighard, T. S. et al. "Bridging the Gap Between Supercritical Fluid Extraction and Liquid Extraction Techniques: Alternative Approaches to the Extraction of Solid and Liquid Environmental Matrices", *Critical Reviews in Analytical Chemistry*, 26(2&3), 61-99, (1996).

Righetti, P. G. et al. "Study of haptoglobin-hemoglobin Complexes by Titration Curves, Capillary Electrophoresis and Capillary Isoelectric Focusing", *J. Chromatogr. A*, 767, 255-262 (1997).

Rosenfeld, J. "Gas Chromatography Profiling in Biomedical Investigations" in *Chemical Analysis: Gas Chromatography*, Clement, R. E. (ed.), 111, 181-215 (1990).

Rotzsche, H. "Chemically Bonded Stationary Phases" in Stationary Phases in Gas Chromatography , *Journal of Chromatography Library*, vol. 48, 142-159, (1991), Elsevier.

Schomburg, G. et al. "Alkylpolysiloxane Glass Capillary Columns Combining High Temperature Stability of the Stationary Liquid and Deactivation of the Surface; Thermal Treatment of Dealkalinized Glass Surfaces by the Stationary Liquid Itself", *Chromatographia*, 12(10), 651-660, (1979).

Schutjes, C. P.M. et al. "Deactivation and Coating of Non-Polar 50 μm I.D. Capillary Columns", *J. Chromatogr.*, 279, 49-57 (1983).

Shen, Y. et al. "High-Efficiency Capillary Isoelectric Focusing of Peptides", *Anal. Chem.*, 72, 2154-2159, (2002).

Shende, C. et al. "Sol-Gel Poly(ethylene Glycol) Stationary Phase for High-Resolution Capillary Gas Chromatography", *Anal. Chem.*, 75, 3518-3530 (2003).

Shihabi, Z. K. "Stacking and Discontinuous Buffers in Capillary Zone Electrophoresis", *Electrophoresis*, 21, 2872-2878 (2000).

Shihabi, Z. K. "Stacking in Capillary Zone Electrophoresis", *J. Chromatogr. A.*, 902, 107-117 (2000).

Shihabi, Z. K. "Transient Pseudo-Isotachophoresis for Sample Concentration in Capillary Electrophoresis", *Electrophoresis*, 23, 1612-1617 (2002).

Shihabi, Z. K. et al. "Insulin Stacking in Capillary Zone Electrophoresis", *J. Chromatogr. A.*, 807, 129-133 (1998).

Spanik, I. et al. "Use of Full-Column Imaging Capillary Isoelectric Focusing for the Rapid Determination of the Operating Conditions in the Preparitive-Scale Continuous Free Flow Isoelectric Focusing Separation of Enantiomers", *J. Chromatogr. A.*, 960, 241-246 (2002).

Stark, F. O. et al. "The Interactions between Trialkylsilanes and E-Glass or Aerosil Surfaces. Reactions of Trimethylsilanol, Trimethylchlorosilane, and Hexamethyldisilazane", *The Journal of Physical Chemistry*, 72(8), 2750-2754, (1968).

Strausbauch, M. A. et al. "Mechanism of Peptide Separation by Solid Phase Extraction Capillary Electrophoresis at Low pH", *Anal. Chem.*, 68, 306-314 (1996).

Sumpter, S.R. et al. "Static Coating of 5 to 50 µm I.D. Capillary Columns for open Tubular Column Chromatography", *J. Chromatogr.*, 517, 503-519 (1990).

Sun, P. et al. "Chitosan Coated Capillary with Reserved Electroosmotic Flow in Capillary Electrophoresis for the Separation of Basic Drugs and Proteins", *J. Microcol. Sep.*, 6, 403-407 (1994).

Toussaint, B. et al. "Enantiomeric Separation of Clenbuterol by transient Isotachophoresis-capillary zone Electophoresis-UV Detection New Optimization Technique for Transient Isotachophoresis", *J. Chromotogr. A.* 173-180(2000).

Tu, C. et al. "Determination of Nitrate in Seawater by Capillary Zone Electophoresis with Chloride-Induced Sample Self-Stacking", *J. Chromatogr. A.*, 966, 205-212 (2002).

Van Der Vlis, E. et al "Combined liquid-liquid electroextraction and isotachophoresis as a fast on-line focusing step in capillary electrophoresis", *Journal of Chromatography A*, 687, 333-341 (1994).

Veraart, J. B. et al. "At-Line Solid-Phase Extraction Coupled to Capillary Electrophoresis: Determination of Amphoteric Compounds in Biological Samples", *J. High Resol. Chromatogr.*, 22, 183-187 (1999).

Vorotilov, K. A. et al. "ORMOSIL Films: Properties and Microelectronic Applications" *Journal of Sol-Gel Science and Technology*, 8, 581-584, (1997).

Wang, D. et al. "Preparation and GC Performance of Sol-Gel Technology-Based Open Tubular Columns" *Eighteenth International Symposium on Capillary Chromatography*, vol. I, May 20-24, 1996, pp. 505-513.

Wang, D. et al., "Sol-Gel Column Technology for Single-Step Deactivation, Coating, and Stationary-Phase Immobilization in High-Resolution Capillary Gas Chromatography", *Anal. Chem.*, 69, 4566-4576 (1997).

Wang, Z. et al. "High-performance polyethylene glycol-coated solid-phase microextraction fibers using sol-gel technology" *Journal of Chromatography A*, 893, 157-168, (2000).

Wei, W. et al. "One-Step Concentration of Analytes Based on Dynamic Change in pH in Capillary Zone Electrophoresis", *Anal. Chem.*, 74, 934-940 (2002).

Welsch, T. et al. "The Thermal Immobilization of Hydroxy-Terminated Silicone Phases in High-Temperature-Silylated Glass Capillaries. A Study of Reaction Mechanisms", *Journal of High Resolution Chromatography*, 14, 153-159, (1991).

Wercinski, S.A.S. et al. "Solid Phase Microextraction Theory" in *Solid Phase Microextraction, a Practical Guide*, 1999, 1-26, Marcel Dekker, Inc., New York.

Wilkes, G. L. et al. " 'Ceramers': Hybrid Materials Incorporating Polymeric/Oligomeric Species into Inorganic Glasses Utilizing a Sol-Gel Approach", *Polymer Preprints* 26(2), 300-302 (1985).

Woolley, C. L. et al. "Deactivation of Fused Silica Capillary Columns with Polymethylhydrosiloxanes", *J. High Resol. Chromatogr./ Chromatogr. Comm.*, 7, 329-332 (1984).

Wu, J. et al. "Polypyrrole-Coated Capillary Coupled to HPLC for In-Tube Solid-Phase Microextraction and Analysis of Aromatic Compounds in Aqueous Samples", *Anal. Chem.*, 73, 55-63, (2001).

Wu, J. et al. "Polypyrrole-Coated Capillary In-Tube Solid Phase Microextraction Coupled with Liquid Chromatography-Electrospray Ionization Mass Spectrometry for the Determination of β-Blockers in Urine and Serum Samples", *J. Microcolumn Separations*, 12(4), 255-266, (2000).

Wu, J. et al. "Speciation of Organoarsenic Compounds by Polypyrrole-Coated Capillary In-Tube Solid Phase Microextraction Coupled With Liquid Chromatograph/Electrospray Ionization Mass Spectrometry", *Analytica Chimica Acta*, 424, 211-222 (2000).

Yakabe, Y. et al. "Immobilization Method for Polyethylene Glycol Using a Cross-linking Co-agent", *J. Chromatogr.*, 558, 323-327 (1991).

Yang, H. et al. "Sample Stacking in Laboratory-on-a-chip Devices", *J. Chromatogr. A.*, 924, 155-163 (2001).

Zapf, A. et al. "GC Analysis of Organic Acids and Phenols Using On-Line Methylation with Trimethylsulfonium Hydroxide and PTV Solvent Split Large Volume Injection", *J. High Resol. Chromotogr.*, 22, 83-88 (1999).

\* cited by examiner (A) Cross-sectional view (500×)  (B) Surface view (10000×)

Deactivated, wall bonded sol-gel TiO$_2$-PDMS coating

TITANIA-BASED COATING FOR CAPILLARY MICROEXTRACTION

CROSS REFERENCE TO RELATED APPLICATION

This application claims the benefit of priority under 35 U.S.C. §119(e) of U.S. Provisional Application Ser. No. 60/521,901, filed Jul. 19, 2004, which is incorporated herein by reference.

GOVERNMENT RIGHTS

This work was supported in part by a grant from the US Naval office (N00014-98-1-0848). Accordingly, the government has certain rights in this invention.

FIELD OF INVENTION

The present invention relates to analytical separation and extraction technology. More specifically, the present invention relates to separation and extraction columns for use in separating, extracting and/or concentrating analytes in a sample.

BACKGROUND OF INVENTION

Solid-phase microextraction (SPME), a solvent-free sample preparation technique, was developed by Pawliszyn and co-workers using a fused-silica fiber externally coated with a polymeric sorbent covering a small segment of it at one of the ends. Analytes present in the sample medium were directly extracted and preconcentrated by the coated sorbent in the process of reaching an extraction equilibrium with the sample matrix. The preconcentrated analytes were then desorbed into a GC instrument for analysis.

In conventional fiber-based SPME, still there exist a number of shortcomings that need to be overcome. These include inadequate thermal and solvent stability of conventionally prepared sorbent coatings, low sample capacity, difficulties associated with the immobilization of thick coatings, susceptibility of the fiber (especially the coated end) to mechanical damage and technical difficulties associated with the hyphenation of fiber-based SPME with liquid-phase separation techniques.

Capillary microextraction (CME) (also called in-tube SPME) presents a convenient format for coupling SPME to HPLC and for automated operation of SPME-HPLC. Hyphenation of CME to HPLC is especially important for the analysis of a wide range of less volatile or thermally labile compounds that are not amenable to GC separation. In the open tubular format of CME, a sorbent coating is applied to the inner surface of a capillary. This alternative format provides an effective solution to the problem associated with the mechanical damage of sorbent coating frequently encountered in conventional fiber-based SPME where the coating is applied on the outer surface of the fiber. In this new format of SPME, a segment of wall-coated capillary GC column is commonly used for the direct extraction of organic analytes from an aqueous medium. To perform HPLC analysis, the extracted analytes are transferred to the HPLC column by desorbing them with an appropriate mobile phase.

Capillary microextraction has great prospects in liquid-phase trace analysis. However, to achieve its full analytical potential, the technology needs further improvements in a number of areas. First, segments of GC columns that are commonly used for sample preconcentration have thin coatings that limit the sorption capacity, and hence, the extraction sensitivity of in-tube SPME. Second, the sorbent coatings in such microextraction capillaries usually are not chemically bonded to capillary inner walls, which limits their thermal and solvent stabilities. Third, conventionally prepared GC coatings that are used in in-tube SPME capillaries inherently possess poor pH stability. This places serious limitations on the range of applications amenable to CME-HPLC analysis. Low pH stability of in-tube SPME coatings practically excludes the applicability of the technique to high-pH samples or analytes that require high-pH solvent systems for desorption from the microextraction capillary. Therefore, development of methodologies for the creation of high pH- and solvent-resistant sorbent coatings is an important area in the future development of in-tube SPME, which is expected to play a major role in effective hyphenation of this sample preconcentration technique with liquid-phase separation techniques that commonly use organo-aqueous mobile phases with a wide range of pH conditions.

Sol-gel chemistry has been recently applied to solid-phase microextraction (SPME) and capillary microextraction (CME) to create silica-based hybrid organic-inorganic coatings. The sol-gel technique provided chemically bonded coatings on the inner surface of fused-silica capillaries, and easily solved the coating stability problems described above.

Although sol-gel technique helped overcome some significant shortcomings of SPME or in-tube SPME techniques by providing an effective means of chemical immobilization for sorbent coatings, an important problem inherent in silica-based material systems (commonly used in SPME or CME) still remains to be solved: silica-based materials possess a narrow window of pH stability. In the context of SPME, it pertains to the stability of silica-based fibers and coatings. The development of alternative materials possessing superior pH stability and better mechanical strength should provide SPME with additional ruggedness, and versatility.

Recently, titania has attracted interest in separation science due to its superior pH stability and mechanical strength compared with silica. Several studies have been conducted on the application of titania in chromatographic separations. Tani et al. reported the preparation of titania-based packing materials for HPLC by sol-gel method, and investigated their properties. Tsai et al. prepared silica capillaries coated with titania or alumina for capillary electrophoresis (CE) separation of proteins. Fujimoto used a thermal decomposition technique to create titania coatings on the inner surface of fused-silica capillaries for capillary zone electrophoresis (CZE) and capillary electrochromatography (CEC) applications. The titania-coated capillaries were found to possess a bi-directional electroosmotic flow (EOF) and low solubility in aqueous solutions within a pH range of 3-12. Pesek et al. reported the surface derivatization of titania with triethoxysilane to prepare titania-based stationary phases via silanization/hydrosilylation. Some other groups reported preparations of silica-coated titania monolayers for faster and more efficient coating, which is important for further preparation of nanocomposites.

We disclose the preparation of sol-gel $TiO_2$-PDMS coated capillaries and show the possibility of on-line CME-HPLC operation using sol-gel $TiO_2$-PDMS microextraction capillaries to provide a significant improvement in pH stability and extraction sensitivity.

SUMMARY OF INVENTION

One aspect of the present invention is directed at methods of making a sol-gel titania-based coatings. The method includes the steps of mixing two or more suitable sol-gel precursors to form a sol-gel solution, hydrolyzing the sol-gel solution to form hydrolyzed products, polycondensating the hydrolyzed products to form a sol-gel network, incorporating chemically the remainder of the two or more sol-gel precursors in the sol-gel network and surface bonding the sol-gel network to a substrate to form a surface bonded sol-gel coating thereon. The first of the two or more sol-gel precursors in the mixing step is titanium (IV) isopropoxide. In certain embodiments of the present invention a second of the two or more sol-gel precursors is polydimethylsiloxane (PDMS). Additionally, in certain other embodiments of the method of making a sol-gel titania-based coatings, the method will include the step of deactivating residual silanol groups on the sol-gel coating with a deactivating agent. Deactivating reagents used in the deactivating step can include hexamethyidisilazane (HMDS) and polymethylhydrosiloxane (PMHS). In certain advantageous embodiments the ratio of HMDS to PMHS is about 4:1 (v:v). It is also found to be advantageous in certain embodiments to perform the deactivating step at elevated temperatures during column conditioning. The mixing step can utilize a chelating agent to decelerate the sol-gel formation. The chelating agent can include acetic acid, trifluoroacetic acid and metal beta-diletonates. The mixing step can further include adding an additional catalyst selected from the group consisting of acids, bases or fluorides. Finally, in certain embodiments it is found advantageous to perform the hydrolyzing and polycondensating steps within the sol-gel solution in proximity to the inner walls of a capillary tube.

The present invention also provides for a microextraction capillary for the preconcentration of trace analytes in a sample. The microextraction capillary has a tube structure and an inner surface. The inner surface is further characterized by the presence of a sol-gel titania-based coating. The sol-gel titania-based coating forms the stationary phase for the microextraction of the analytes. The microextraction capillary with the sol-gel titania-based coating can be made from two or more sol-gel precursors where the first of the two or more sol-gel precursors is titanium (IV) isopropoxide. In certain embodiments of the present invention it is found advantageous to utilize PDMS as a second of the two or more sol-gel precursors. In certain embodiments of the present invention it is also found advantageous to have the inner surface of the capillary composed of fused silica. It is further found advantageous to chemically bond the sol-gel titania-based coating to the fused-silica inner surface of the capillary. The microextraction capillary can include an outer surface having a protective coating to prevent against breakage of the capillary. The protective coating can be a polyimide protective coating. A further advantageous embodiment of the present invention provides a sol-gel titania-based coating that is at least about 250 μm in thickness. The sol-gel titania-based coating advantageously possesses pH stability and retains extraction performance after prolonged treatment with a NaOH solution.

The present invention further provides for a method of making a titania-based sol-gel coated capillary for microextraction of analytes in a sample medium. The method includes the steps of preparing a sol solution comprising titanium (IV) isopropoxide, processing the sol solution to form a sol-gel extraction medium, filling a capillary with the sol-gel extraction medium wherein the sol-gel extraction medium chemically binds to the inner walls of the capillary to form a titania-based sol-gel coated capillary and purging the capillary of unbound sol-gel extraction medium. In certain advantageous embodiments the method will include PDMS as a sol-gel precursor in the sol solution. It is also found advantageous in certain embodiments to have the capillary remain filled with the sol-gel extraction media for at least about 15 minutes to facilitate the formation of a surface bonded sol-gel coating before the unbound sol-gel extraction medium is purged. The step of purging the capillary of unbound sol-gel extraction medium can be performed by applying helium pressure of about 20 psi for at least about 30 minutes. Lastly, the method of making a titania-based sol-gel coated capillary for microextraction of analytes in a sample medium can advantageous include the step of conditioning the titania-based sol-gel coated capillary in an oven using temperature-programmed heating wherein the heat increments upward from about 40° C. to about 320° C. at an increment of about 1° C./minute followed by a holding at about 320° C. for about 3 hours. The step of thermal conditioning can further include cooling the titania-based sol-gel coated capillary to room temperature following the 3 hour holding, rinsing the capillary with methylene chloride and methanol and reheating using temperature-programmed heating wherein the heat increments upward from about 40° C. to about 320° C. at an increment of about 1° C./minute followed by a holding at about 320° C. for about 30 minutes.

BRIEF DESCRIPTION OF THE DRAWINGS

For a fuller understanding of the nature and objects of the invention, reference should be made to the following detailed description, taken in connection with the accompanying drawings, in which.

acetonitrile/water (isocratic elution), respectively; 1 mL/min flow rate; UV detection at 254 nm; ambient temperature.

Figure 8:
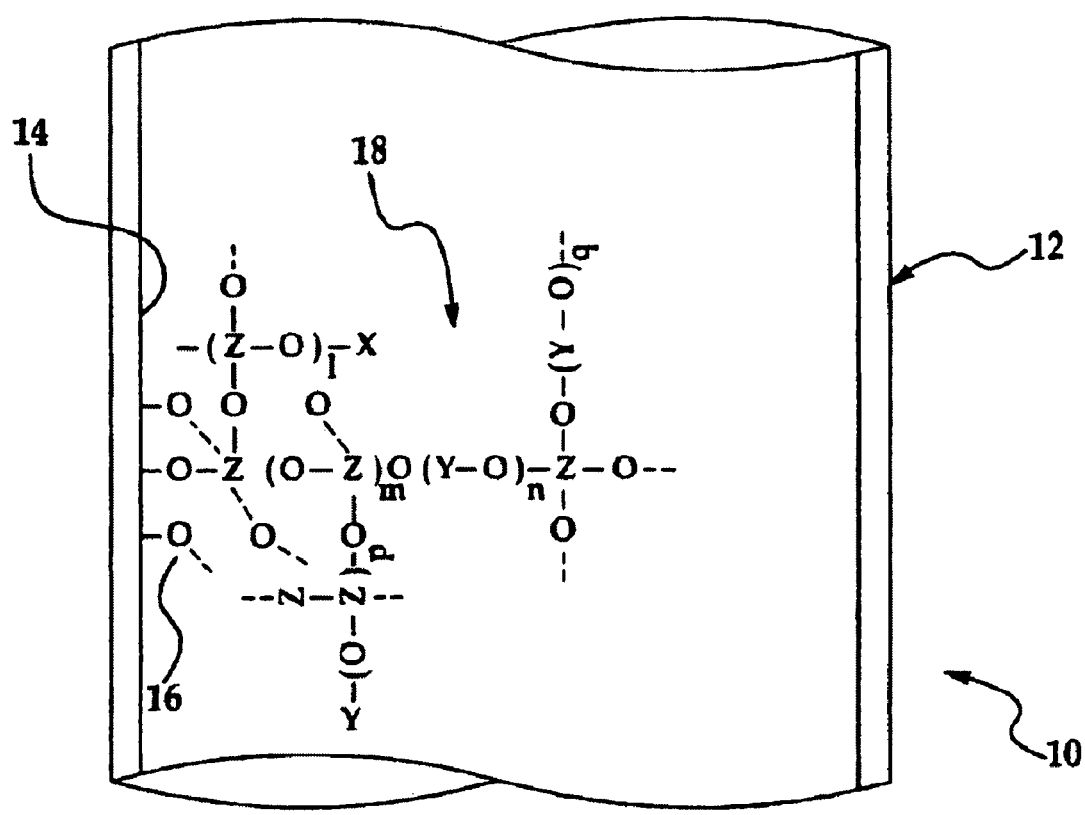

FIG. 8. A longitudinal, cross-section view of a capillary column having a surface-bonded sol-gel network.

Figure 9:
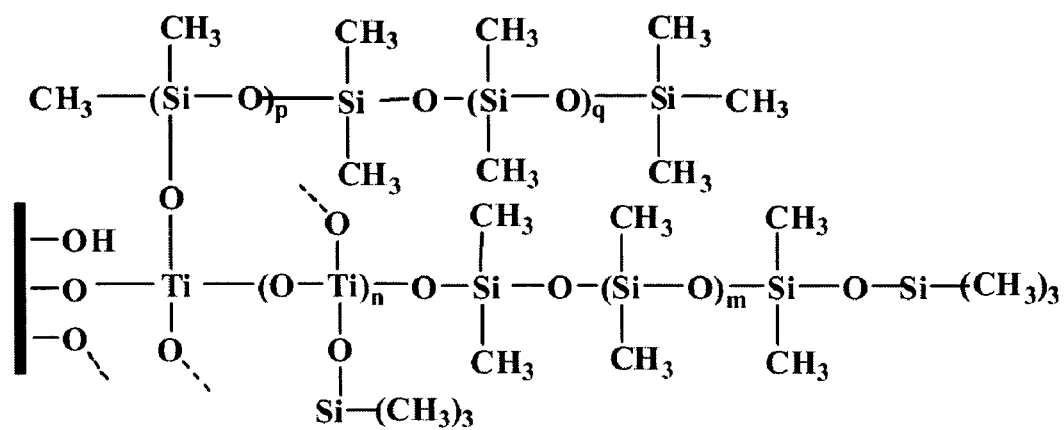

FIG. 9. Illustration of surface-bonded sol-gel TiO2-PDMS network on the fused silica capillary inner walls.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is understood that other embodiments may be utilized and structural changes made without departing from the scope of the invention.

Sol-gel titania-poly (dimethylsiloxane) (TiO2-PDMS) coating was developed for capillary microextraction (CME) to perform on-line preconcentration and HPLC analysis of trace impurities in aqueous samples. A method is presented describing in situ preparation of the titania-based sol-gel PDMS coating and its immobilization on the inner surface of a fused silica microextraction capillary. To perform CME-HPLC, the sol-gel TiO2-PDMS capillary was installed in the HPLC injection port as an external sampling loop, and a conventional ODS column was used for the liquid chromatographic separation. The target analytes were extracted on-line for by passing the aqueous sample through this sampling loop.

The sol-gel titania-PDMS coated capillaries were used for on-line extraction and HPLC analysis of polycyclic aromatic hydrocarbons, ketones, and alkylbenzenes. The extracted analytes were then transferred to the HPLC column using an organic-rich mobile phase followed by HPLC separation via gradient elution. To our knowledge, this is the first report on the use of sol-gel titania-based organic-inorganic material as a sorbent in capillary microextraction.

The newly developed sol-gel titania-based CME coatings demonstrated excellent pH stability and enhanced extraction capability over the commercial GC coatings that are conventionally used for the same purpose. Extraction characteristics of a sol-gel titania-PDMS capillary remained practically unchanged after continuous rinsing with a 0.1 M NaOH solution (pH=13) for 12 hours.

Sol-gel TiO2-PDMS coated microextraction capillaries possess excellent pH stability and retain their extraction characteristics intact even after prolonged treatment with highly alkaline (pH=13) NaOH solution. Direct chemical bonding of the coating to capillary inner walls provides these coatings with excellent solvent resistance, and make sol-gel TiO2-PDMS coated capillaries very much suitable for on-line sample preconcentration in CME-HPLC analysis. The newly developed sol-gel TiO2-PDMS coating was effectively used for the extraction of different classes of analytes with good extraction sensitivity, and run-to-run repeatability. Low ppb and sub-ppb level (0.15 ppb-11.60 ppb) detection limits were achieved for PAHs, ketones, and alkylbenzenes in CME-HPLC analysis using the newly constructed sol-gel TiO2-PDMS coated microextraction capillary in conjunction with UV detection. Through proper optimization of experimental conditions for sol-gel coating and the capillary microextraction processes it should be possible to further enhance the extraction sensitivity. For volatile and thermally stable analytes, use of sol-gel TiO2-PDMS coated capillaries in CME-GC provides significant enhancement in sensitivity.

The present invention provides a high pH-resistant, surface-bonded sol-gel titania coatings for capillary microextraction, facilitating the effective hyphenation of CME with HPLC. Judicious utilization of unique attributes of sol-gel chemistry allowed the creation of a surface-bonded hybrid organic-inorganic titania coating on the inner walls of a fused silica capillary providing an opportunity for the judicious utilization of the attributes of sol-gel chemistry to exploit advanced material properties of titania-based sorbents in capillary microextraction. Unlike the conventional multi-step coating technology, the sol-gel approach involves a single-step procedure to accomplish the sorbent coating, its chemical immobilization, and deactivation.

As sol-gel precursors, titanium alkoxides differ significantly from silicon alkoxides in terms of their chemical reactivity and complex-forming ability. These differences dictate the adoption of different strategies for the creation of titania-based sol-gel sorbents compared with those for silica-based analogs. While sol-gel reactions in a silica-based system is rather slow and often requires the use of catalysts to accelerate the process, titania-based (transition metal oxide-based in general) sol-gel reactions are very fast. This is explained by the fact that titanium alkoxides are very reactive toward nucleophilic reagents like water. They readily undergo hydrolysis which results in a very fast sol-gel process. Because of this, titania-based sol-gel reactions need to be decelerated by a suitable means to allow for the sol-gel process to be conducted in a controlled manner. This is usually accomplished through the use of suitable chelating agents that form complexes with the sol-gel precursors (or replace the reactive alkoxy group with a less reactive group), thus hindering their participation in the sol-gel reactions. Without such a chelating agent, the gelation takes place instantaneously as the sol-gel solution ingredients are mixed together. Chelating agents such as acetic acid, trifluoroacetic acid, or metal beta-diketonates are often used for this purpose.

Sol-gel TiO2-PDMS coated capillaries were prepared through hydrolytic polycondensation reactions performed within fused silica capillaries followed by thermal conditioning of the created coatings to achieve fine porous structures. TFA served as a chelating agent, and decelerated the gelation process for the creation of TiO2-PDMS coating. It has been shown by infra-red spectra that the acetate ion can serve as a bidentate ligand (chelating and bridging) to the transition metal alkoxides, such as $Ti(OR)_4$ or $Zr(OR)_4$.

Figure 2:
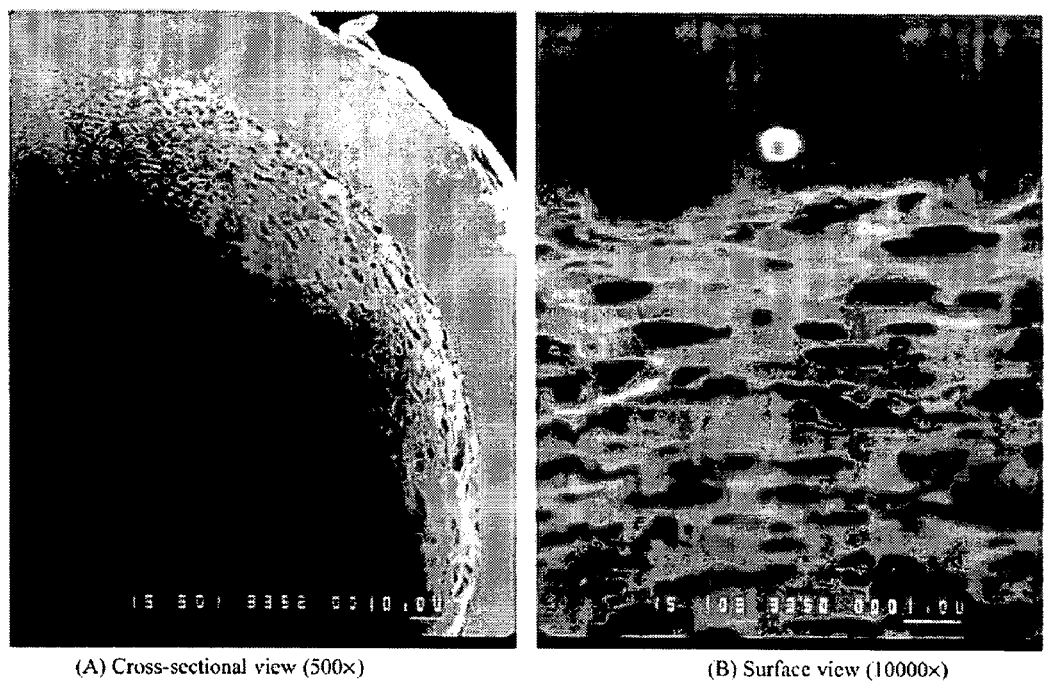
FIG. 2. Scanning electron microscopic images of a 320-μm i.d. fused silica capillary with sol-gel TiO2-PDMS coating: (A) cross-sectional view (500×) and (B) surface view (10000×).

FIG. 2 presents two scanning electron micrographs (SEM) showing the fine structural features of a 320-μm i.d. fused silica capillary with sol-gel TiO2-PDMS coating on the inner surface. As is evident from these images, the sol-gel TiO2-PDMS coating in the microextraction capillary acquires a porous structure, providing enhanced surface area and sorption ability. Based on the SEM data, the thickness of the sol-gel TiO2-PDMS coating was estimated at ~0.5 μm. These images also show remarkable coating thickness uniformity in the sol-gel TiO2-PDMS coated microextraction capillaries.

The sol-gel process for the generation and chemical immobilization of the coating involves: (A) hydrolysis of the titanium alkoxide precursor, (B) polycondensation of the hydrolysis products into a three-dimensional sol-gel network, (C) chemical incorporation of hydroxy-terminated PDMS in the sol-gel network, and (D) chemical anchoring of the sol-gel hybrid polymer to the inner walls of the capillary. Scheme 1 illustrates the hydrolysis and polycondensation reactions of the sol-gel precursor, titanium (IV) isopropoxide, and scheme 2 represents the final structure of the sol-gel TiO2-PDMS coating on the inner surface of a fused silica capillary.

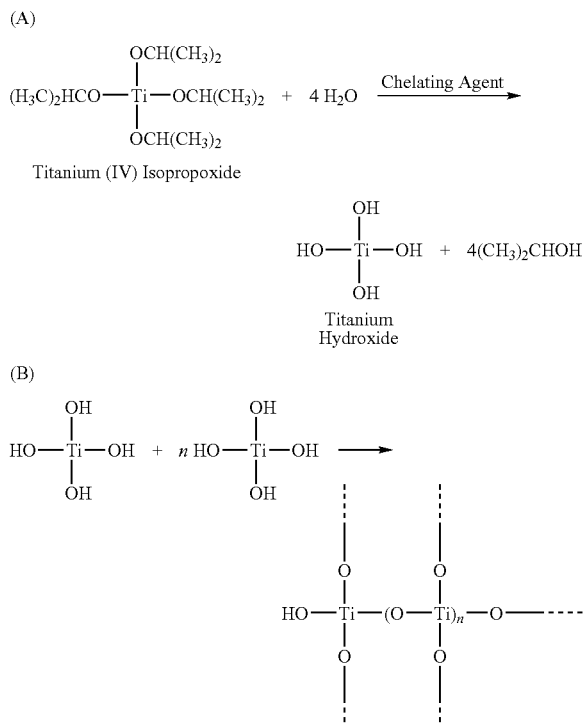

Scheme 1. (A) Hydrolysis of titanium (IV) isopropoxide, and (B) Polycondensation of hydrolyzed titanium hydroxide

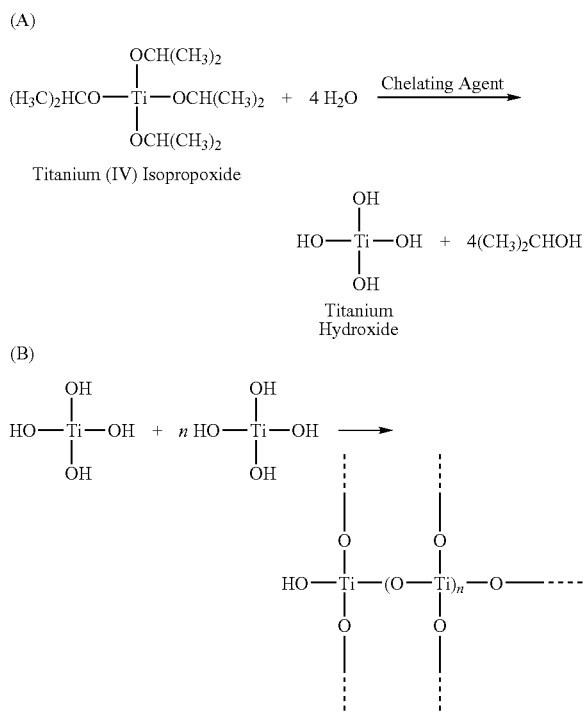

Figure 3:
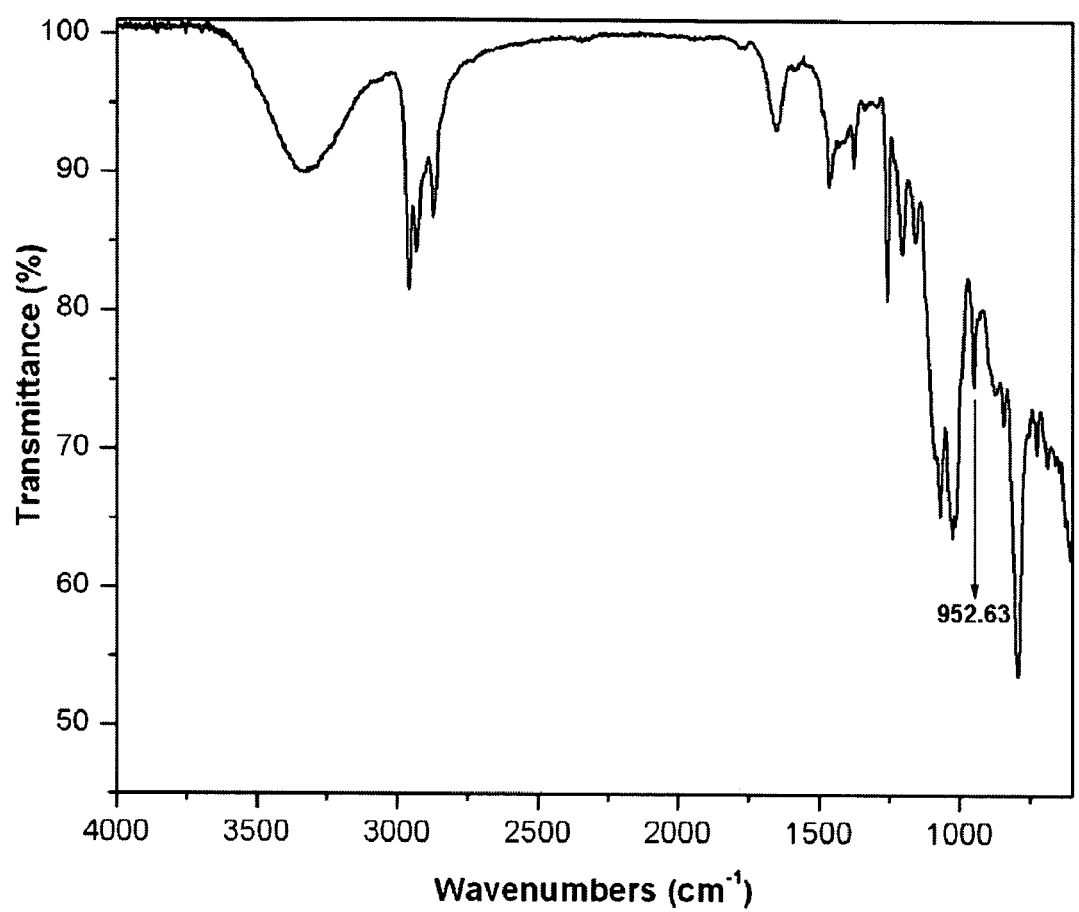
FIG. 3. FT-IR spectra of the sol-gel Ti-PDMS coating

Scheme 1. (A) Hydrolysis of titanium (IV) isopropoxide, and (B) Polycondensation of hydrolyzed titanium hydroxide The formation of Ti—O—Si bonds in the prepared sol-gel sorbent was examined by FT-IR. The FTIR experiments were performed by passing IR radiation through a thin layer of sol-gel titania coating material that was used in the fused silica capillary. This was done in separate experiments outside the fused silica capillary. It has been reported that a characteristic IR band representing Si—O—Ti bonds is located at 940-960 cm$^{-1}$. FIG. 3 shows FT-IR spectra of the sol-gel Ti-PDMS coating with a specific band at 952.63 cm$^{-1}$. This is indicative of the presence of Si—O—Ti bonds in the sol-gel sorbent used in the fused silica microextraction capillaries to perform on-line CME-HPLC analysis.

Deactivation of the sol-gel coatings can be expected to take place mainly during thermal conditioning of the capillary, through derivatization of the free hydroxyl groups in the coating structure with HMDS and PMHS incorporated in the sol solution. To control the gelation time and to obtain a transparent gel, it was essential to find an optimum ratio (v/v) of HMDS and PMHS. In the present study this ratio was found to be 4:1 (HMDS:PMHS, v/v).

Sol-gel technology is quite versatile, and allows for the control of coating thickness either by manipulating the reaction time or composition of the sol solution. Zeng et al. has recently reported the preparation of 70-μm thick silica-based sol-gel coating on conventional SPME fiber. It should be possible to create such thick coatings (either silica-based or transition metal oxide-based) on the inner surface of fused silica capillaries as well. Use of thicker coatings should enhance the sample capacity and extraction sensitivity in CME with titania-based sol-gel coatings.

The sol-gel titania-PDMS coatings demonstrated excellent pH stabilities over conventionally created coatings like those used in commercial GC capillary columns. FIG. 4 illustrates the CME performance of a TiO2-PDMS coated microextraction capillary in CME-HPLC analysis of PAHs before (FIG. 4a) and after (FIG. 4b) rinsing the capillary with a 0.1 M NaOH solution (pH=13) for 12 h. Analogously obtained data for a piece of DB-5 GC column are presented in FIG. 4c and FIG. 4d, respectively. Chromatogram 4b (FIG. 4b) was obtained on the sol-gel TiO2-PDMS coated microextraction capillary after it was thoroughly rinsed with deionized water. The extraction of PAHs was performed under the same set of conditions as in the FIG. 4a. From the comparison of peak profiles and peak heights in FIGS. 4a and 4b, it is evident that the sol-gel TiO2-PDMS coating in the microextraction capillary remained unaffected even after the prolonged rinsing with 0.1 M NaOH solution of pH 13.

Figure 4A:
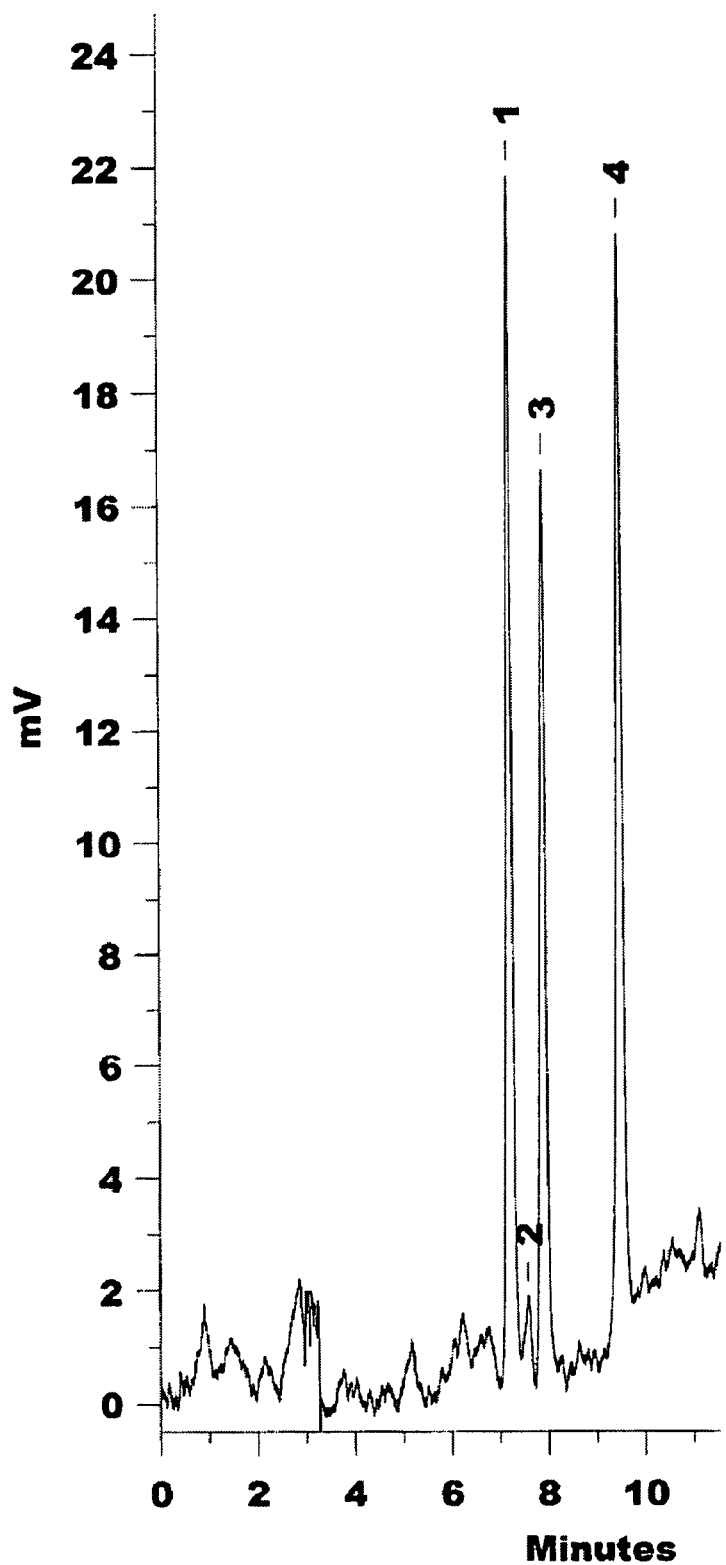
FIG. 4. Chromatograms representing capillary microextraction-HPLC analysis of PAHs using sol-gel titania-PDMS coated (4a and 4b) and commercial DB-5 (4c and 4d) capillaries before (4a and 4c) and after (4b and 4d) rinsing the microextraction capillaries with a 0.1 M NaOH solution (pH=13) for 12 h. Extraction conditions: 40-cm (0.25 mm i.d.×0.25 μm sol-gel TiO2-PDMS-coated capillary (4a and 4b), and 40-cm (0.25 mm i.d.×0.25 μm commercial GC capillary (4c and 4d); extraction time, 40 min (gravity feed at room ambient temperature). Other conditions: 25 cm×4.6 (m i.d. ODS column (5 (m dp); gradient elution with mobile phase composition programmed from 80:20 (v/v) acetonitrile/water to 100% acetonitrile for 20 min; 1 mL/min flow rate; UV detection at 254 nm; ambient temperature. Peaks: (1) Acenaphthylene (500 ppb), (2) Fluorene (100 ppb), (3) Phenanthrene (20 ppb), and (4) Fluoranthene (100 ppb).
Figure 4B:
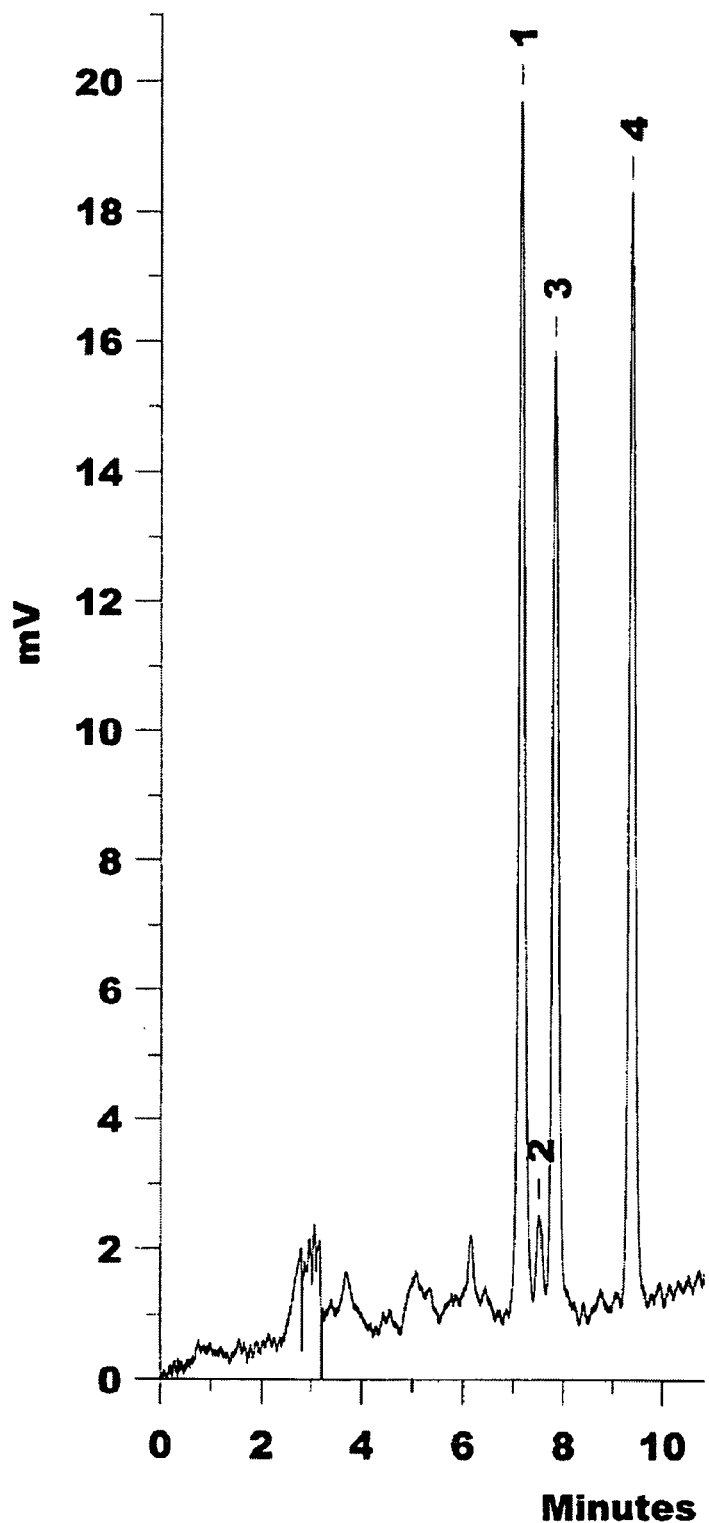
Figure 4C:
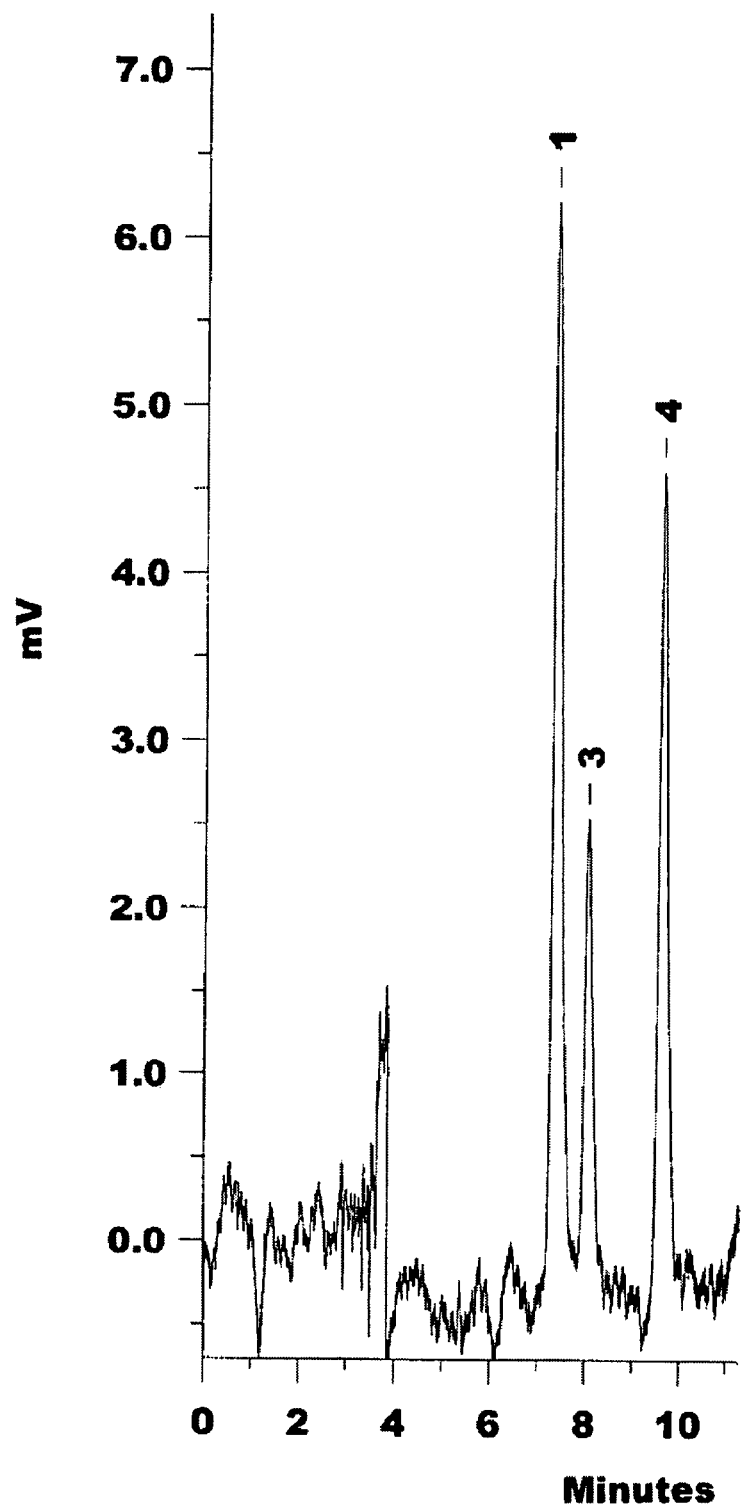
Figure 4D:
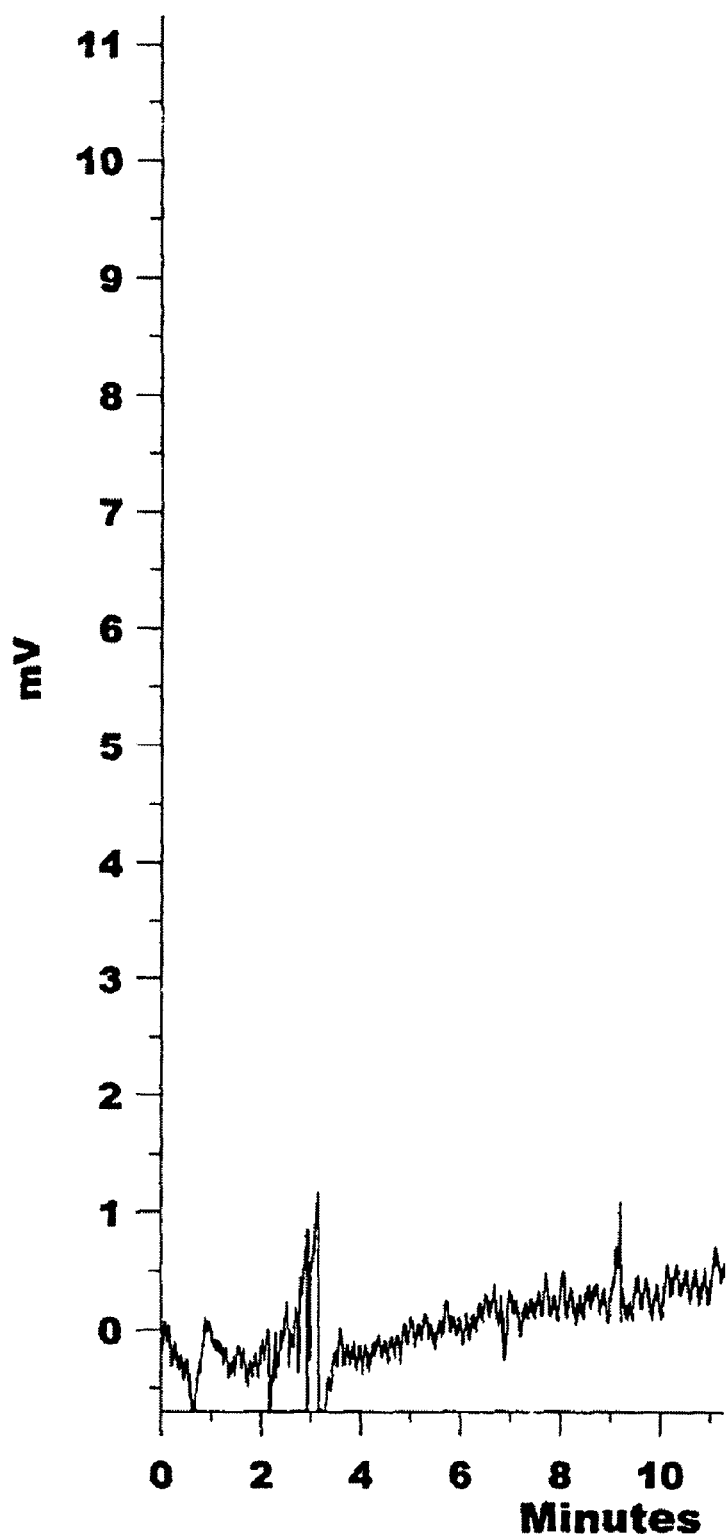

On the other hand, the stationary phase coating in the commercial GC capillary showed significantly less extraction sensitivity as is evident from peak heights in FIG. 4c. It also failed to survive the harsh conditions of rinsing with 0.1 M NaOH solution, which is evidenced by a dramatic decrease in the extraction sensitivity after the NaOH treatment (compare FIG. 4c and FIG. 4d). These results show that a sol-gel TiO2-PDMS coated capillary possesses excellent pH stability and retains its extraction ability under extreme pH conditions, while conventionally prepared GC coatings were found to be unstable under such extreme pH conditions.

Table 1 shows repeatability and detection limit data for CME-HPLC analysis using sol-gel TiO2-PDMS coated microextraction capillaries. Less than 9% RSD in peak area and detection limits in the range of 0.18~3.72 ppb were achieved using UV-detection.

TABLE 1

Peak area repeatability and detection limit data for PAHs using a sol-gel TiO$_2$—PDMS-coated capillary treated with 0.1 M NaOH for 12 hours

| | Peak area repeatability (n = 3) | | | | % Change in Peak Area $\left|\frac{A_2 - A_1}{A_1}\right| \times 100\%$ | Detection limits | |
|---|---|---|---|---|---|---|---|
| | Before Rinsing | | After Rinsing | | | Before Rinsing | After Rinsing |
| Extracted PAHs | Mean peak area (A$_1$) (Arbitrary unit) | RSD (%) | Mean peak area (A$_2$) (Arbitrary unit) | RSD (%) | | S/N = 3 (ppb) | S/N = 3 (ppb) |
| Acenaphthylene | 23.5 | 9.5 | 23.9 | 0.5 | 2.1 | 3.07 | 3.72 |
| Phenanthrene | 19.8 | 8.8 | 20.6 | 8.9 | 3.9 | 0.15 | 0.18 |
| Fluoranthene | 21.4 | 9.7 | 21.2 | 6.0 | 0.6 | 0.84 | 0.89 |

Figure 5:
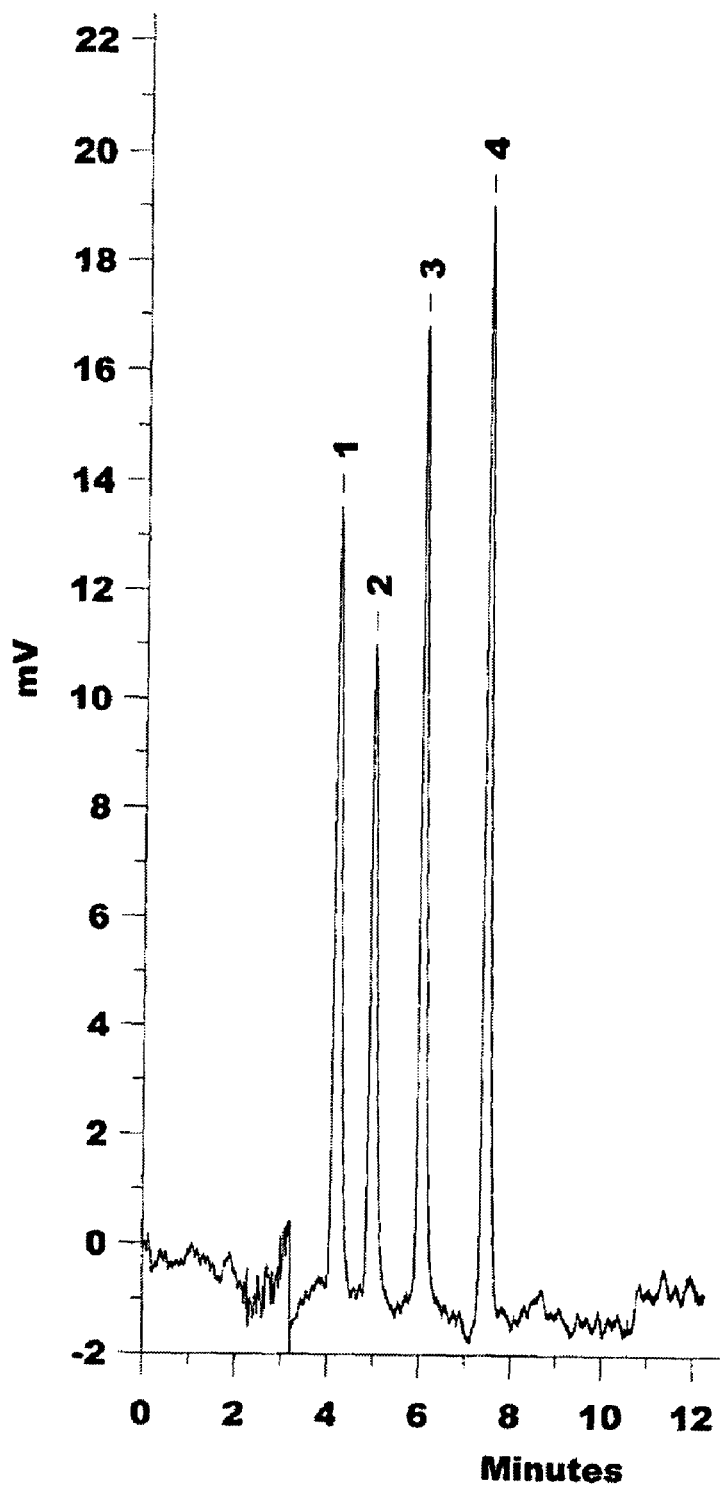
FIG. 5. Capillary microextraction-HPLC analysis of ketones. Extraction conditions: 40-cm (0.32 mm i.d. sol-gel TiO2-PDMS-coated capillary; extraction time, 40 min (gravity feed at room ambient temperature). Other conditions: 25 cm×4.6 (m i.d. ODS column (5 (m dp); gradient elution with mobile phase composition programmed from 80:20 (v/v) acetonitrile/water to 100% acetonitrile for 15 min; 1 mL/min flow rate; UV detection at 254 nm; ambient temperature. Peaks: (1) Butyrophenone (1 ppm), (2) Valerophenone (1 ppm), (3) Hexanophenone (500 ppb), and (4) Heptanophenone (300 ppb).

FIG. 5 presents a chromatogram illustrating CME-HPLC analysis of moderately polar aromatic ketones extracted from an aqueous sample using a sol-gel coated TiO2-PDMS capillary.

Compared to PAHs samples (FIG. 4a), ketones needed higher analyte concentrations (300 ppb-1 ppm) for CME-HPLC analysis. This may be explained by the nonpolar nature of the sol-gel TiO2-PDMS coating, higher solubility of ketones in water due to higher polarity, and the working principles of UV detection. In this case, the run-to-run peak area repeatability was less than 8% RSD. Detection limits for the extracted ketones ranged between 2.47 ppb for heptanophenone to 11.60 ppb for valerophenone in conjunction with UV detection. From the presented results it is evident that sol-gel TiO2-PDMS coating is able to extract both nonpolar and moderately polar analytes with good extraction sensitivity. The ability of instant sol-gel coating may be due to the presence of two different types of domains (a nonpolar organic domain based on PDMS and a more polar inorganic domain based on sol-gel titania materials) in such coatings.

Figure 6:
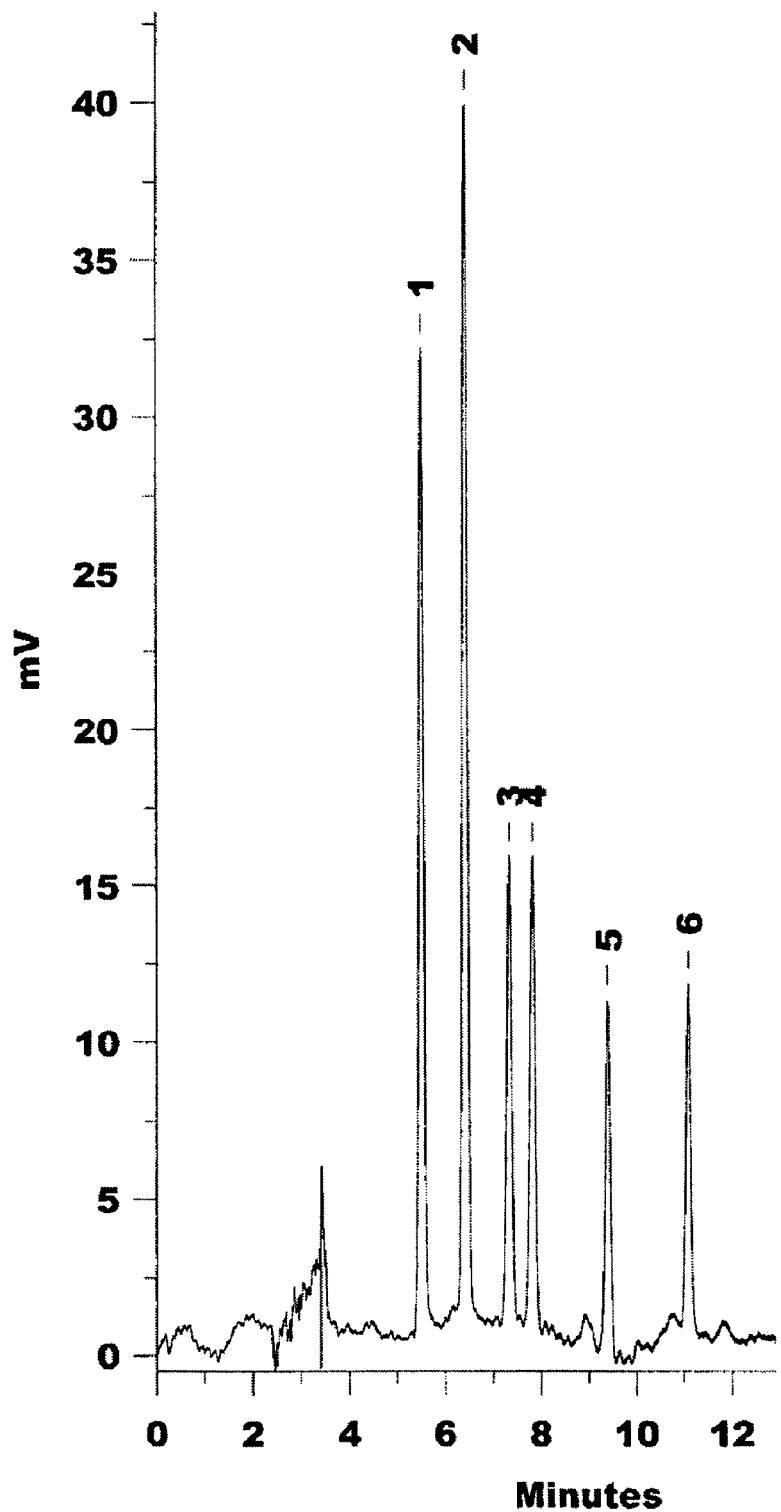
FIG. 6. Capillary microextraction-HPLC analysis of alkylbenzenes. Extraction conditions are the same as in the FIG. 5. Other conditions: 25 cm×4.6 (m i.d. ODS column (5 (m dp); gradient elution with mobile phase composition programmed from 80:20 acetonitrile/water to 100% acetonitrile for 15 min; 1 mL/min flow rate; UV detection at 205 nm; ambient temperature. Peaks: (1) Toluene (600 ppb), (2) Ethyl benzene (200 ppb), (3) Cumene (50 ppb), (4) Propylbenzene (50 ppb), (5) Butylbenzene (50 ppb), and (6) Amylbenzene (50 ppb).

FIG. 6 illustrates on-line CME-HPLC analysis of alkylbenzenes using a TiO2-PDMS coated capillary. Excellent detection limits were also achieved for these analytes (0.65-5.45 ppb), using UV detection. Like PAHs, alkylbenzenes are less polar analytes than aromatic ketones, and they are well extracted by a sol-gel TiO2-PDMS extraction capillary with low ppb and sub-ppb level detection limits. Table 2 summarizes the peak area repeatability and detection limit data for PAHs, ketones, and alkylbenzenes.

Figure 7:
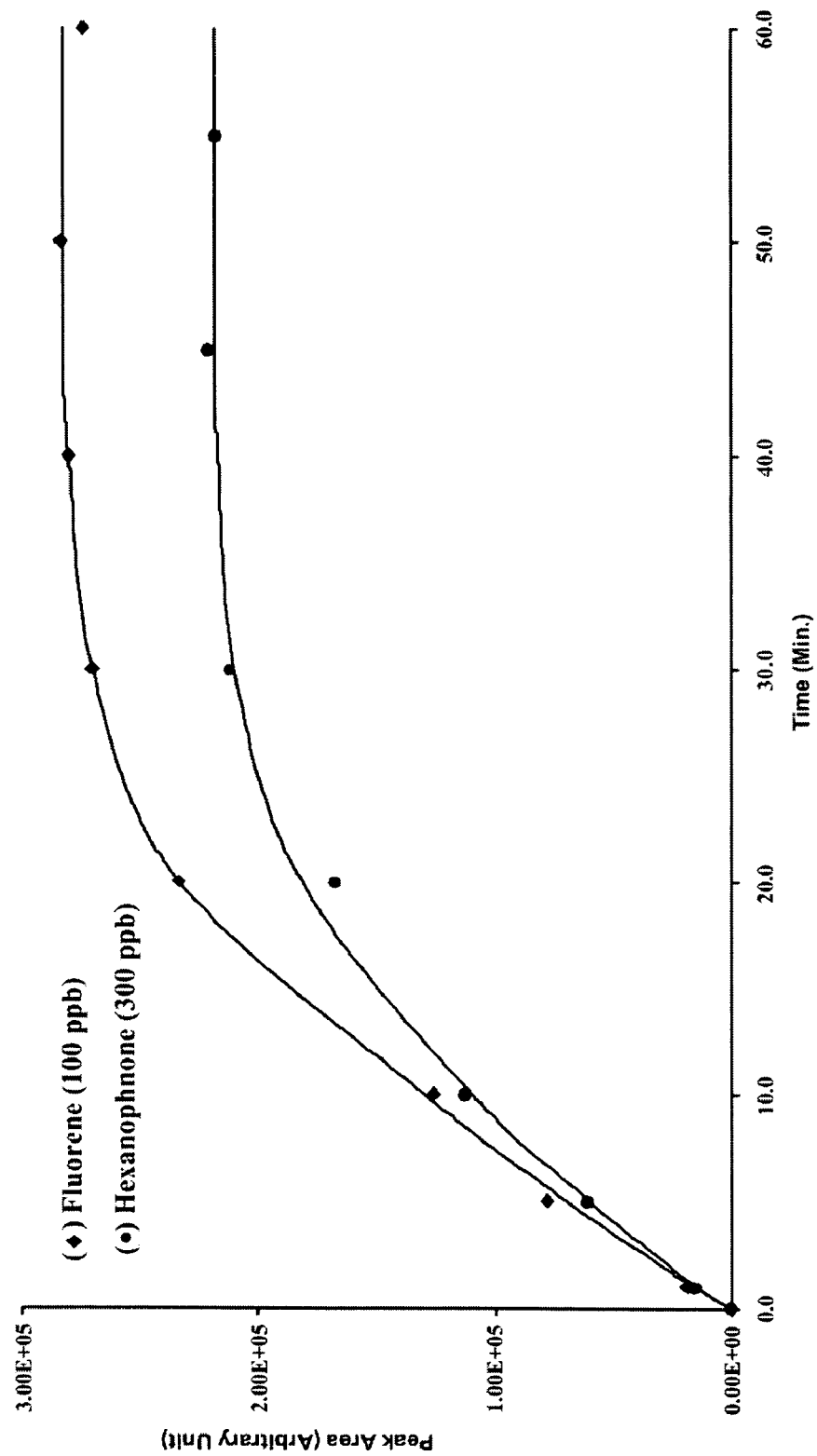
FIG. 7. Illustration of the extraction kinetics of fluorene (( ), and hexanophenone (( )obtained on a 40 cm (0.32 mm i.d. sol-gel TiO2-PDMS-coated capillary using 100 ppb and 300 ppb aqueous solutions, respectively. Extraction conditions are the same as in the FIG. 5. Other conditions: 25 cm×4.6 (m i.d. ODS column (5 (m dp.); 85:15 (v/v), and 90:10 (v/v)

FIG. 7 illustrates the extraction kinetic profile for: (A) fluorene (nonpolar analyte) and (B) hexanophenone (moderately polar analyte) on a sol-gel TiO2-PDMS coated microextraction capillary.

TABLE 2

Peak area repeatability and detection limit data for PAHs, ketones, and alkylbenzenes using a sol-gel TiO$_2$—PDMS-coated capillary

| Chemical class | Name | Peak area repeatability (n = 3) | | Detection limits S/N = 3 (ppb) |
|---|---|---|---|---|
| | | Mean peak area (Arbitrary unit) | RSD (%) | |
| PAH | Acenaphthylene | 23.5 | 9.5 | 3.07 |
| | Fluorene | 12.2 | 8.9 | 1.40 |
| | Phenanthrene | 19.8 | 8.8 | 0.15 |
| | Fluoranthene | 21.4 | 9.7 | 0.84 |
| Ketone | Butyrophenone | 48.6 | 3.9 | 9.62 |
| | Valerophenone | 27.7 | 4.6 | 11.60 |
| | Hexanophenone | 27.9 | 3.5 | 4.35 |
| | Heptanophenone | 21.6 | 7.9 | 2.47 |
| Alkylbenzene | Toluene | 20.2 | 1.9 | 5.45 |
| | Ethylbenzene | 23.9 | 1.6 | 1.24 |
| | Cumene | 12.3 | 6.1 | 0.74 |
| | Propylbenzene | 13.6 | 4.5 | 0.65 |
| | Butylbenzene | 14.4 | 9.9 | 0.84 |
| | Amylbenzene | 94.9 | 7.4 | 1.07 |

Experimental data for these curves representing extraction kinetic profiles were obtained by individually performing capillary microextraction for each of the solutes. The microextraction experiments were performed using aqueous samples containing 100 ppb and 300 ppb concentrations of fluorene and hexanophenone, respectively. A series of capillary microextraction experiments were conducted to vary the extraction time for each of the two analytes that were extracted from their standard solutions. Three replicate extractions of each analyte were performed for 1-, 5-, 10-, 20-, 30-, 40-, 50-, and 60 min. The average peak area was then plotted against the extraction time to obtain the data as presented in FIG. 7. For both fluorene and hexanophenone, extraction equilibrium was reached within 40 min as is evidenced by the plateau on the extraction curve. Since PDMS has nonpolar characteristics, the TiO2-PDMS coating tends to extract a nonpolar analyte, in this case fluorene, better than a more polar analyte, hexanophenone, which has higher affinity for the aqueous medium.

Optimization of capillary preparation methodologies and operation conditions allow the full analytical potential of the sol-gel titania coated extraction capillaries to be achieved. Use of TiO2-PDMS extraction capillary in CME-GC will likely exhibit improved detection limits, since CME-GC allows for the use of highly sensitive flame ionization detector. The use of wider bore capillaries with thicker sol-gel coatings or monolithic extraction beds should further enhance the extraction sensitivity.

Sol-gel capillary microextraction techniques as presently described have great potential for automated operation in hyphenation with both gas-phase and liquid-phase separation techniques. Because of the tubular format of the extraction device combined with high thermal and solvent stability of the surface-bonded sol-gel extraction coating, sol-gel capillary microextraction can be expected to offer high degree of versatility in automated operation.

A sol-gel has the general formula:

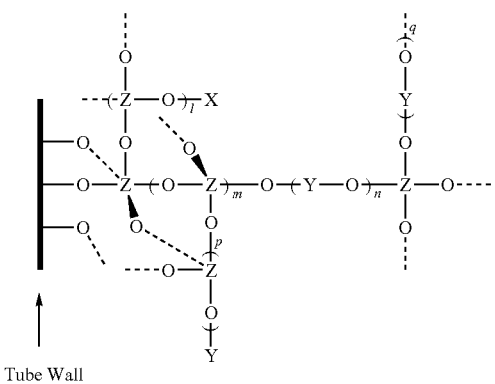

Tube Wall wherein,

X=Residual of a deactivation reagent (e.g., polymethylhydrosiloxane (PMHS), hexamethyldisilazane (HMDS), etc.);

Y=Sol-gel reaction residual of a sol-gel active organic molecule (e.g., hydroxy terminated molecules including polydimethylsiloxane (PDMS), polymethylphenylsiloxane (PMPS), polydimethyldiphenylsiloxane (PDMDPS), polyethylene glycol (PEG) and related polymers like Carbowax 20M, polyalkylene glycol such as Ucon, macrocyclic molecules like cyclodextrins, crown ethers, calixarenes, alkyl moieties like octadecyl, octyl, etc.

Z=Sol-gel precursor-forming chemical element (e.g. Si, Al, Ti, Zr, etc.)

l=An integer≧0;
m=An integer≧0;
n=An integer≧0;
p=An integer≧0;
q=An integer≧0; and l, m, n, p, and q are not simultaneously zero.

Dotted lines indicate the continuation of the chemical structure with X, Y, Z, or Hydrogen (H) in space.

Various sol-gel reagent systems are known in the art. A sol-gel solution will typically include two or more sol-gel precursors, a deactivation reagent, one or more solvents and, in the case of silica-based sol-gels, a catalyst. The sol-gel precursor generally contains a chromatographically active moiety selected from the group consisting of octadecyl, octyl, cyanopropyl, diol, biphenyl, phenyl, cyclodextrins, crown ethers and other moieties. Representative precursors include, but are not limited to: Methyltrimethoxysilane, Tetramethoxysilane, 3-(N-styrylmethyl-2-aminoethylamino)-propyltrimethoxysilane hydrochloride, N-tetradecyidimethyl(3-trimethoxysilylpropyl)ammonium chloride, N(3-trimethoxysilylpropyl)-N-methyl-N,N-diallylammonium chloride, N-trimethoxysilylpropyltri-N-butylammonium bromide, N-trimethoxysilylpropyl-N,N,N-trimethylammonium chloride, Trimethoxysilylpropylthiouronium chloride, 3-[2-N-benzyaminoethylaminopropyl]trimethoxysilane hydrochloride, 1,4-Bis(hydroxydimethylsilyl)benzene, Bis(2-hydroxyethyl)-3-aminopropyltriethoxysilane, 1,4-bis(trimethoxysilylethyl)benzene, 2-Cyanoethyltrimethoxysilane, 2-Cyanoethyltriethoxysilane, (Cyanomethylphenethyl)trimethoxysilane, (Cyanomethylphenethyl)triethoxysilane, 3-Cyanopropyldimethylmethoxysilane, 3-Cyanopropyltriethoxysilane, 3-Cyanopropyltrimethoxysilane, n-Octadecyltrimethoxysilane, n-Octadecyldimethylmethoxysilane, Methyl-n-Octadecyldiethoxysilane, Methyl-n-Octadecyltrimethoxysilane, n-Octadecyltriethoxysilane, n-Dodecyltriethoxysilane, n-Dodecyltrimethoxysilane, n-Octyltriethyoxysilane, n-Octyltrimethoxysilane, n-Ocydiisobutylmethoxysilane, n-Octylmethyidimethoxysilane, n-Hexyltriethoxysilane, n-isobutyltriethoxysilane, n-Propyltrimethoxysilane, Phenethyltrimethoxysilane, N-Phenylaminopropyltrimethoxysilane, Styrylethyltrimethoxysilane, 3-(2,2,6,6-tetramethylpiperidine-4-oxy)-propyltriethoxysilane, N-(3-triethoxysilylpropyl)acetyl-glycinamide, (3,3,3-trifluoropropyl)trimethoxysilane, and (3,3,3-trifluoropropyl)methyidimethoxysilane, and any other similar precursor known to those of skill in the art. Sol gel technology is taught in U.S. Pat. Nos. 6,759,126 B1 and 6,783,680 B2 and U.S. Patent Application Publication Nos. US 2002/0150923 A1, US 2003/0213732 A1, US 2004/0129141 A1 and US 2005/0106068 A1, the contents of which are incorporated herein by reference.

The invention will be further described by way of the following non-limiting example.

EXAMPLE

Development and Characterization of the Microextraction Capillary Having Surface-bonded Sol-gel Titania Coating 1. Equipment On-line CME-HPLC experiments were carried out on a Micro-Tech Scientific (Vista, Calif.) Ultra Plus HPLC system with a variable wavelength UV detector (Linear UVIS 2000). A Nicolet model Avatar 320 FT-IR (Thermo Nicolet, Madison, Wis.) was used for FT-IR measurements. A reversed-phase ODS column (25 cm×4.6 mm i.d., 5 µm $d_p$) was used for HPLC separation of the extracted analytes. A Fisher model G-560 Vortex Genie 2 system (Fisher Scientific) was used for thorough mixing of the sol solutions. A Microcentaur model APO 5760 centrifuge (Accurate Chemical and Scientific Corp., Westbury, N.Y.) was used for centrifugation of sol solutions. A Barnstead model 04741 Nanopure deionized water system (Barnstead/Thermodyne, Dubuque, Iowa) was used to obtain ~16.0 MΩ-cm water. On-line data collection and processing were done using Chrom-Perfect (version 3.5) for Windows computer software (Justice Laboratory Software, Denville, N.J.).

2. Chemicals and Materials

Fused silica capillary (250- and 320 µm i.d.) was purchased from Polymicro Technologies Inc. (Pheonix, Ariz.). A commercial GC column (DB-5, 30 m×0.25 mm i.d., 0.25 µm film thickness) was purchased from J&W Scientific (Folsom, Calif.). Titanium (IV) isopropoxide (99.999%), 1-butanol (99.4+ %), Poly(methylhydrosiloxane) (PMHS), 1,1,1,3,3,3-hexamethyidisilazane (HMDS), trifluoroacetic acid (TFA), polycyclic aromatic hydrocarbons (PAHs) (acenaphthylene, fluorene, phenanthrene, fluoranthene), ketones (butyrophenone, valerophenone, hexanophenone, heptanophenone), and alkylbenzenes (toluene, ethylbenzene, cumene, propylbenzene, butylbenzene, amylbenzene) were purchased from Aldrich (Milwaukee, Wis.). Hydroxy-terminated poly (dimethylsiloxane) (PDMS) was purchased from United Chemical Technologies, Inc. (Bristol, Pa.). HPLC-grade solvents (acetonitrile, methylene chloride, and methanol) were purchased from Fisher Scientific (Pittsburgh, Pa.).

3. Preparation of the Sol Solution

The sol solution was prepared by thoroughly vortexing the following reagents in a 2-mL polypropylene centrifuge tube: a sol-gel-active organic component (hydroxy-terminated PDMS, 50 mg), a sol-gel precursor (titanium (IV) isopropoxide, 50 μL), two solvents (methylene chloride and 1-butanol, 200 μL each), a mixture of two surface deactivation reagents (HMDS, 8 μL and PMHS, 2 μL), and a sol-gel chelating agent (27% TFA in H2O, 18 μL). The content of the tube was then centrifuged for 5 min (at 13,000 rpm; 15,682 g). Finally the top clear solution was transferred to another clean vial by decantation, and was further used for coating the fused silica microextraction capillary.

4. Preparation of Sol-gel TiO2-PDMS Coated Microextracion Capillaries

A 1-m long hydrothermally treated fused silica capillary (250- or 320 μm i.d.) was installed on an in-house built gas pressure-operated capillary filling/purging device, and the capillary was filled with the prepared sol solution under 10 psi helium pressure. After filling, the sol solution was kept inside the capillary for 15 min to facilitate the creation of a surface-bonded coating due to sol-gel reactions taking place in the coating solution inside the capillary. Following this, the unbonded portion of the sol solution was expelled from the capillary under helium pressure (20 psi), and the capillary was further purged with helium for 30 min. The coated capillary was then conditioned in a GC oven by programming the temperature from 40° C. to 320° C. at 1 (C/min under helium purge. The capillary was held at 320° C. for 180 min. Finally, the capillary was cooled down to room temperature and rinsed with methylene chloride and methanol (3 mL each). Following this, the capillary was installed in the GC oven for drying and further thermal conditioning under temperature-programmed heating as described above, except that this time the capillary was held at the final temperature for 30 min.

5. Capillary Microextraction (CME) and On-line CME-HPLC Analysis

Figure 1:
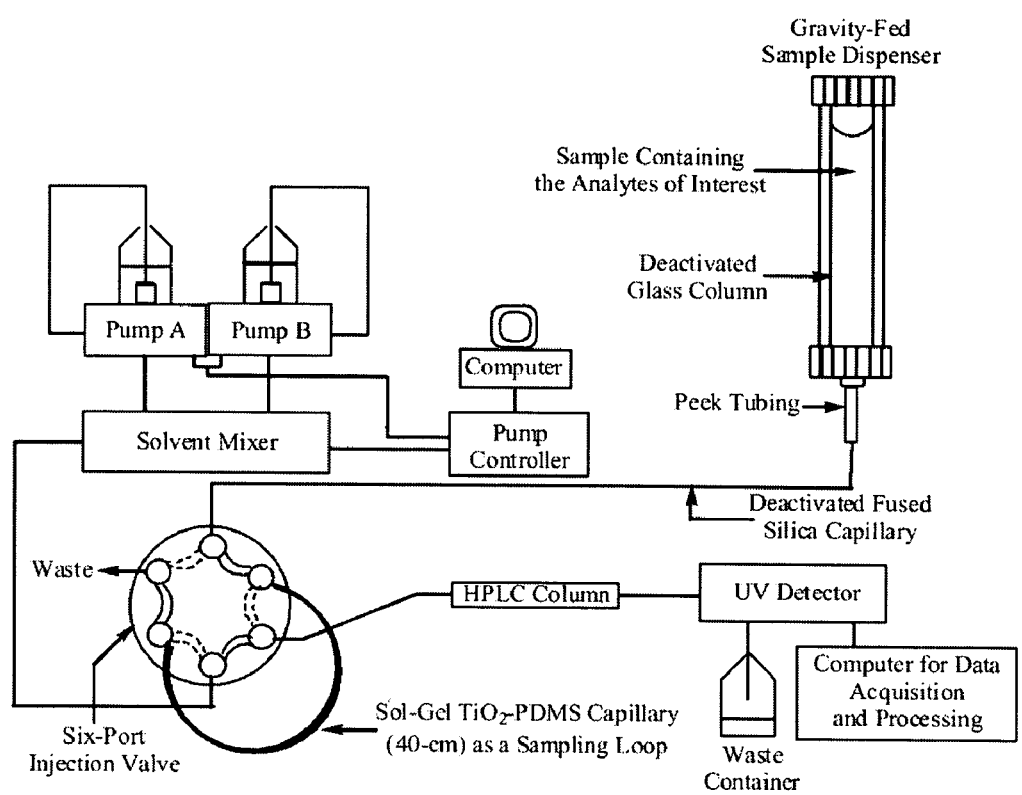
FIG. 1. Schematic diagram of the on-line CME-HPLC setup.

A schematic of the CME-HPLC setup for on-line capillary microextraction and HPLC analysis is presented in FIG. 1. An ODS column (25 cm×4.6 mm i.d., 5 μm dp) was previously installed in the HPLC system and pre-equilibrated with the mobile phase consisting of a mixture of acetonitrile and water (80:20, v/v). A 40-cm segment of the sol-gel TiO2-PDMS coated microextraction capillary was mounted on the injection port as an external sampling loop. Analytes were preconcentrated in the sol-gel TiO2-PDMS coating by passing the aqueous sample from a gravity-fed dispenser through this sol-gel titania-PDMS coated microextraction capillary for 40 min. Using a syringe, the sampling loop was flushed out with deionized water to remove the sample matrix. The analytes extracted in the sol-gel TiO2-PDMS coating of the sampling loop were then transferred into the HPLC column by desorbing with 100% acetonitrile for 30 seconds. This was accomplished by simply switching the injection valve from the "load" to "inject" position. The injected analytes were then separated on the ODS column under gradient elution conditions by programming acetonitrile composition in the organo-aqueous mobile phase from 80% (v/v) to 100% in 15 min.

6. Treatment of Coated Capillaries With 0.1 M NaOH Solution

A 40-cm segment of the sol-gel TiO2-PDMS coated capillary was directly installed on the gravity-fed sample dispenser, and continuously rinsed with 0.1 M NaOH solution (pH=13) for 12 hours. The capillary was then flushed out with deionized water for 30 minutes, and mounted back on the HPLC injection port. The target analytes (PAHs) were extracted on-line for 40 min, followed by their HPLC analysis as described in 2.5.

Using the same procedure a 40-cm segment of the commercial GC capillary (DB-5) was treated with a 0.1 M NaOH solution. CME performances of the used capillaries were evaluated both before and after the alkaline treatment to explore pH stability of the used coatings.

7. Safety Precautions

The presented work involved the use of various chemicals (organic and inorganic) and solvent that might be environmentally hazardous with adverse health effects. Proper safety measures should be taken in handling strong bases and organic solvents such as methanol, methylene chloride, and acetonitrile. All used chemicals must be disposed in the proper waste containers to ensure personnel and environmental safety.

REFERENCES

Arthur, C. L. and J. Pawliszyn, *Anal. Chem.* 62 (1990) 2145.

Belardi, R. G. and J. Pawliszyn, *Water Pollut. Res. J. Can.* 24 (1989) 179.

Bigham, S., J. Medlar, A. Kabir, C. Shende, A. Alli and A. Malik, *Anal Chem.* 74 (2002) 752.

Blomberg, L. G., *J. Microcolumn Sep.* 2 (1990) 62.

Boccuti, M. R., K. M. Rao, A. Zecchina, G. Leofanti, and G. Petrini, *Stud. Surf Sci. Catal.* 48 (1989) 133.

Bouche, J. and M. Verzele, *J. Gas Chromatogr.* 6 (1968) 501.

Boyd-Boland, A. A. and J. Pawliszyn, *Anal. Chem.* 68 (1996) 1521.

Bradley, D. C., R. C. Mehrotra and D. P. Gaur, *Metal Alkoxides*, Academic Press, London, 1978.

Brennan, A. B. and G. L. Wilkes, *Polymer* 32 (1991) 733.

Brinker, C. J. and G. W. Scherer, *Sol-Gel Science: The Physics and Chemistry of Sol-Gel Processing*, Academic Press, New York, N.Y. 1990.

Chen, J. and J. Pawliszyn, *Anal. Chem.* 67 (1995) 2530.

Chen, Q., N. Miyata, T. Kokubo and T. Nakamura, *J. Biomed. Mater. Res.* 51 (2000) 605.

Chong, S. L., D. Wang, J. D. Hayes, B. W. Wilhite and A. Malik, *Anal. Chem.* 69 (1997) 3889.

Doeuff, S., M. Henry, C. Snachez and J. Livage, *J. Non-Cryst. Solids* 89 (1987) 206.

Dutoit, D. C. M., M. Shneider and A. Baiker, *J. Catal.* 153 (1995) 165.

Eisert, R. and J. Pawliszyn, *Anal. Chem.* 69 (1997) 3140.

Emili, M., L. Incoccia, S. Mobilio, G. Fagherazzi and M. Guglielmi, *J. Non-Cryst. Solids* 74 (1985) 11.

Fadeev, A. Y., R. Helmy and S. Marcinko, *Langmuir* 18 (2002) 7521.

Fadeev, A. Y. and T. J. McCarthy, *J. Am. Chem. Soc.* 121 (1999) 12184.

Fujimoto, C., *Electrophoresis,* 23 (2002) 2929.

Glajch, J. L., J. J Kirkland and L. Kohler, *J. Chromatogr.* 384 (1987) 81.

Haridas, M. M., S. Datta and J. R. Bellare, *Ceram. Int.* 25 (1999) 601.

Hayes, J. D. and A. Malik, *Anal. Chem.* 72 (2000) 4090.

Hayes, J. D. and A. Malik, *J. Chromatogr. B* 695 (1997) 3.

Hayes, J. D., Ph.D. Dissertation, University of South Florida, USA, 2002.

Iler, R. K., *J. Colloid Interf. Sci.* 55 (1976) 25.

Jiang, J.-T. and Y.-M. Zuo, *Anal. Chem.* 73 (2001) 686.

Jinno, K., T. Muramatsu, Y. Saito, Y. Kiso, S. Magdic and J. Pawliszyn, *J. Chromatogr. A* 754 (1996) 137.

Kataoka, H. and J. Pawliszyn, *Chromatographia.* 50 (1999) 532.

Kawahara, M., H. Nakamura and T. Nakajima, *J. Chromatogr.* 515 (1990) 149.

Kirkland, J. J., J. L. Glajch and R. D. Farlee, *Anal. Chem.* 61 (1989) 2.

Livage, J., M. Henry and C. Sanchez, *Prog. Solid St. Chem.* 18 (1988) 259.

Malik, A. and S. L. Chong, In Application of Solid-phase Microextraction; J. Pawliszyn, Ed.; Royal Society of Chemistry: Cambridge, U.K, 1999.

McDevitt, N. T. and W. L. Baun, *Spectrochim. Acta* 20 (1964) 799.

Mehrotra, R. C., R. Bohra and D. P. Gaur, In *Metal-Diketonates and Allied Derivatives*, Academic Press, London (1978).

Moriguchi, I., Y. Tsujigo, Y. Teraoka and S. Kagawa, *J. Phys. Chem. B* 104 (2000) 8101.

Muller, L. T. Gorecki, J. Pawliszyn and J. Fresenius, *Anal. Chem.* 364 (1999) 610.

Pesek, J. J., M. T. Matyska and J. Ramakrishnan, *Chromatographia* 49 (1999) 424.

Poole, C. F., S. K. Poole and In E. Heftmann (Ed.) *Chromatography*, 5th Edition, Part A: Fundamentals and Techniques, Journal of Chromatography Library 51A, Elsevier, Amsterdam, 1992.

Rodriguez, I. and M. P. Llompart, *J. Chromatogr. A* 885 (2000) 291.

Shafi, K. V. P. M., A. Ulman, X. Yan, N.-L. Yang, M. Himmelhaus and M. Grunze, *Langmuir,* 17 (2001), 1726.

Tani, K. and Y. Suzuki, *J. Chromatogr. A,* 722 (1996) 129.

Tellez, L., J. Rubio, F. Rubio, E. Morales and J. L. Oteo, *J. Mater. Sci.* 38 (2003) 1773.

Trudinger, U., G. Muller and K. K. Unger, *J. Chromatogr. A* 535 (1990) 111.

Tsai, P., C.-T. Wu and C. S. Lee, *J. Chromatogr. B* 657 (1994) 285.

Wang, D. X., S. L. Chong and A. Malik, *Anal. Chem.* 69 (1997) 4566.

Wang, Z., C. Xiao, C. Wu and H. Han, *J. Chromatogr. A* 893 (2000) 157.

Wen, J. and J. E. Mark, *J. Appl. Polym. Sci.* 58 (1995) 1135.

Winkler, J. and S. Marme, *J. Chromatogr. A* 888 (2000) 51.

Woodley, C. L., R. C. Kong, B. E. Richter and M. L. Lee, *J. High Resolut. Chromatogr.* Chromatogr. Commun. 7 (1984) 329.

Wu, J. and J. Pawliszyn, *Anal. Chem.* 73 (2001) 55.

Wu, N.-L., S.-Y Wang and I. A Rusakova, *Science* 285 (1999) 1375.

Zeng, Z., W. Qiu, M. Yang, X. Wei, Z. Huang and F. Li, *J. Chromatogr. A* 934 (2001) 51.

Zeng, Z., W. Qiu and Z. Huang, *Anal. Chem.* 73 (2001) 2429.

Zhang, Z. M. J. Yang, and J. Pawliszyn, *Anal. Chem.* 66 (1994) 844A.

What is claimed is:

1. A microextraction capillary for the preconcentration of trace analytes in a sample, the microextraction capillary having a tube structure and an inner surface, the inner surface further comprising a hybrid organic-inorganic sol-gel titania-based coating made from two or more sol-gel precursors, wherein the sol-gel titania-based coating forms the stationary phase for the microextraction of the analytes and wherein the sol-gel titania-based coating is chemically bonded to the fused-silica inner surface of the capillary.

2. The microextraction capillary of claim 1 wherein a first of the two or more sol-gel precursors is titanium (IV) isopropoxide.

3. The microextraction capillary of claim 1 wherein a second of the two or more sol-gel precursors is polydimethylsiloxane (PDMS).

4. The microextraction capillary of claim 1 having an outer surface, the outer surface comprising a protective coating to prevent against breakage of the capillary.

5. The microextraction capillary of claim 1 wherein the sol-gel titania-based coating possesses enhanced pH stability relative to a silica-based coating and retains extraction performance after prolonged treatment with a NaOH solution.

6. The microextraction capillary of claim 1 wherein the sol-gel titania-based coating is at least about 0.25 μm in thickness.

7. The microextraction capillary according to claim 1, wherein the sot-gel titania-based coating comprises $TiO_2$ and PDMS.

* * * * *

UNITED STATES PATENT AND TRADEMARK OFFICE
CERTIFICATE OF CORRECTION

PATENT NO. : 7,622,191 B2
APPLICATION NO. : 11/161005
DATED : November 24, 2009
INVENTOR(S) : Malik et al.

It is certified that error appears in the above-identified patent and that said Letters Patent is hereby corrected as shown below:

Column 3,
Lines 10-11, "hexamethyidisilazane" should read --hexamethyldisilazane--.

Column 4,
Line 59, "Ethyl benzene" should read --Ethylbenzene--.

Column 12,
Lines 7-8, "Methyl-n-Octadecyltrimethoxysilane," should read
    --Methyl-n-Octadecyldimethoxysilane,--.
Line 60, "hexamethyidisilazane" should read --hexamethyldisilazane--.

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,622,191 B2
APPLICATION NO. : 11/161005
DATED : November 24, 2009
INVENTOR(S) : Malik et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 939 days.

Signed and Sealed this

Twenty-sixth Day of October, 2010

David J. Kappos
*Director of the United States Patent and Trademark Office*